US012589208B2

(12) United States Patent
Chabert et al.

(10) Patent No.: US 12,589,208 B2
(45) Date of Patent: Mar. 31, 2026

(54) LUBRICATING SHUTTLE

(71) Applicant: Sanofi Winthrop Industrie, Gentilly (FR)

(72) Inventors: Philippe Chabert, Paris (FR); David Darras, Paris (FR)

(73) Assignee: Sanofi Winthrop Industrie, Gentilly (FR)

( * ) Notice: Subject to any disclaimer, the term of this patent is extended or adjusted under 35 U.S.C. 154(b) by 0 days.

(21) Appl. No.: 18/714,908

(22) PCT Filed: Nov. 30, 2022

(86) PCT No.: PCT/EP2022/083909

§ 371 (c)(1),
(2) Date: May 30, 2024

(87) PCT Pub. No.: WO2023/099594

PCT Pub. Date: Jun. 8, 2023

(65) Prior Publication Data

US 2025/0041523 A1 Feb. 6, 2025

(30) Foreign Application Priority Data

Dec. 1, 2021 (EP) ..................................... 21315260

(51) Int. Cl.
*B05D 1/28* (2006.01)
*A61M 5/31* (2006.01)
*B05C 1/06* (2006.01)
(52) U.S. Cl.
CPC ............. *A61M 5/3129* (2013.01); *B05C 1/06* (2013.01); *A61M 2005/3131* (2013.01); *A61M 2205/0238* (2013.01); *A61M 2207/10* (2013.01)

(58) Field of Classification Search
CPC ....................................................... B05D 1/28
See application file for complete search history.

(56) References Cited

U.S. PATENT DOCUMENTS

| 464,843 | A | 12/1891 | Bagger |
|---|---|---|---|
| 2,763,017 | A | 9/1956 | Redin |
| 3,214,780 | A | 11/1965 | Sharpe |
| 4,010,308 | A | 3/1977 | Wiczer |

(Continued)

FOREIGN PATENT DOCUMENTS

| CN | 107138355 A | 9/2017 |
|---|---|---|
| CN | 109530133 B | 5/2020 |

(Continued)

OTHER PUBLICATIONS

International Preliminary Report on Patentability in International Appln. No. PCT/EP2022/083901, mailed on Jun. 13, 2024, 6 pages.

(Continued)

*Primary Examiner* — Cachet I Proctor
(74) *Attorney, Agent, or Firm* — Fish & Richardson P.C.

(57) ABSTRACT

A method of lubricating a surface of a tubular element for a medicament delivery device includes the steps of moving a device relative to the tubular element for a medicament delivery device, contacting the tubular element with a brush portion of the device, and depositing lubricant agent on the surface of the tubular element to lubricate a surface of the tubular element.

20 Claims, 6 Drawing Sheets

(56) References Cited

U.S. PATENT DOCUMENTS

| | | | | |
|---|---|---|---|---|
| 4,137,623 | A * | 2/1979 | Taylor | B05C 7/08 |
| | | | | 427/230 |
| 4,275,096 | A | 6/1981 | Taylor | |
| 4,603,449 | A * | 8/1986 | Knapp | B08B 9/0557 |
| | | | | 15/104.061 |
| 5,456,940 | A * | 10/1995 | Funderburk | F16N 7/32 |
| | | | | 427/236 |
| 6,165,281 | A * | 12/2000 | Yoon | B08B 1/34 |
| | | | | 15/23 |
| 6,447,610 | B1 * | 9/2002 | Vetter | B05C 7/08 |
| | | | | 427/230 |
| 7,367,151 | B1 | 5/2008 | Black et al. | |
| 8,479,344 | B2 | 7/2013 | Maslanka | |
| 9,220,631 | B2 * | 12/2015 | Sigg | A61M 5/178 |
| RE46,065 | E | 7/2016 | Crawford | |
| 2008/0200101 | A1 * | 8/2008 | Chevallier | B24D 15/04 |
| | | | | 451/340 |
| 2009/0199873 | A1 | 8/2009 | Pruett | |
| 2014/0012227 | A1 * | 1/2014 | Sigg | A61M 5/315 |
| | | | | 604/218 |
| 2017/0008027 | A1 * | 1/2017 | Horn | B05D 1/42 |
| 2020/0264093 | A1 * | 8/2020 | Campbell | G01N 17/04 |
| 2021/0393881 | A1 * | 12/2021 | Foucher | B05D 3/147 |
| 2025/0027605 | A1 | 1/2025 | Chabert et al. | |
| 2025/0027606 | A1 | 1/2025 | Chabert et al. | |
| 2025/0035261 | A1 | 1/2025 | Chabert et al. | |

FOREIGN PATENT DOCUMENTS

| | | | |
|---|---|---|---|
| CN | 112337743 A | 2/2021 | |
| EP | 1072321 A2 | 1/2001 | |
| EP | 1072321 B1 | 1/2006 | |
| EP | 3824926 A1 | 5/2021 | |
| GB | 1242013 A | 8/1971 | |
| GB | 2118671 A | 11/1983 | |
| WO | WO 2010/034004 A1 | 3/2010 | |
| WO | WO 2023/099588 A1 | 6/2023 | |
| WO | WO 2023/099590 A1 | 6/2023 | |
| WO | WO 2023/099594 A1 | 6/2023 | |
| WO | WO 2023/099597 A1 | 6/2023 | |

OTHER PUBLICATIONS

International Preliminary Report on Patentability in International Appln. No. PCT/EP2022/083903, mailed on Jun. 13, 2024, 5 pages.
International Preliminary Report on Patentability in International Appln. No. PCT/EP2022/083909, mailed on Jun. 13, 2024, 6 pages.
International Preliminary Report on Patentability in International Appln. No. PCT/EP2022/083913, mailed on Jun. 13, 2024, 5 pages.
International Search Report and Written Opinion in International Appln. No. PCT/EP2022/083901, mailed on Mar. 14, 2023, 8 pages.
International Search Report and Written Opinion in International Appln. No. PCT/EP2022/083903, mailed on Mar. 13, 2023, 6 pages.
International Search Report and Written Opinion in International Appln. No. PCT/EP2022/083909, mailed on Mar. 14, 2023, 8 pages.
International Search Report and Written Opinion in International Appln. No. PCT/EP2022/083913, mailed on Mar. 15, 2023, 7 pages.
U.S. Appl. No. 18/714,860, filed May 30, 2024, Philippe Chabert.
U.S. Appl. No. 18/714,881, filed May 30, 2024, Philippe Chabert.
U.S. Appl. No. 18/714,897, filed May 30, 2024, Philippe Chabert.

* cited by examiner

LUBRICATING SHUTTLE

CROSS REFERENCE TO RELATED APPLICATIONS

The present application is the national stage entry of International Patent Application No. PCT/EP2022/083909, filed on Nov. 30, 2022, and claims priority to Application No. EP 21315260.6, filed on Dec. 1, 2021, the disclosures of which are incorporated herein by reference.

TECHNICAL FIELD

The present disclosure relates to a method of lubricating an interior surface of a component of a medicament device.

BACKGROUND

Injection devices, for example auto-injectors, typically have a sealed container of medicament, and a needle for injection of the medicament into a patient. In one type of device, the medicament container may comprise a medicament cartridge and the needle may be initially separated from the cartridge. An initial action moves the cartridge and needle together so that the needle pierces the cartridge. In another type of device, the medicament container may comprise a syringe containing a medicament and the needle may be secured to the syringe. In both cases, a plunger or piston within the cartridge or syringe can then be moved into the cartridge or syringe to dispense medicament through the needle for injection to a patient.

In most injection devices, one or more functions require movement of components relative to one another. However, the movements of components relative to one another must overcome frictional forces acting on sliding surfaces in order to function properly. In an attempt to reduce friction, it is known to scrape the surfaces of components to try to make a sliding surface smoother and/or remove obstructions.

SUMMARY

The present disclosure describes an advantageous method of lubricating a surface of a tubular element for a medicament delivery device. The method comprises the steps of moving a device relative to the tubular element, contacting the tubular element with a brush portion of the device, and depositing lubricant on the surface of the tubular element.

This advantageously reduces the coefficient of friction of the tubular element for a medicament delivery device so that a smaller force is required to perform an actuation step when using the medicament delivery device.

In some embodiments, the method may further comprise the step of deforming the brush portion through contact with the tubular element to release the lubricant agent.

Deforming the brush portion may apply pressure to the brush portion and cause the lubricant agent to exude from the brush portion onto the surface of the tubular element.

In some embodiments, the device and tubular element may be moved continuously along an arcuate path about a rotational axis of a lubricating apparatus whilst in contact with each other.

This may provide the advantage that the efficiency of the method is improved by enabling constant and continuous lubrication of a plurality of tubular elements, and even a plurality of tubular elements simultaneously In some embodiments, the moving step may comprise moving the device using a translation movement relative to the tubular element. In some embodiments, the moving step may further comprise moving the device using a rotational movement relative to the tubular element.

This may provide the advantage that the lubricant agent deposited on the surface of the tubular element is wiped around the circumferential surface as the device is moved through the tubular element to provide a more homogeneous layer of lubricant.

In some embodiments, the depositing step may comprise depositing a layer of lubricant on the surface of the tubular element that is in the range of about 40 nm to about 60 nm.

In some embodiments, the step of moving the device may comprise moving the device into a position such that the longitudinal axis of the shaft portion is aligned with the central axis of the tubular element.

In some embodiments, the step of moving the device may comprise moving the device into the tubular element such that the introduction chamfer of the brush portion contacts the surface of the tubular element to align the longitudinal axis of the shaft portion with the central axis of the tubular element.

This may provide the advantage that the device and tubular element are properly aligned to provide a more homogeneous treatment of the inner circumferential surface and to reduce uneven wear on the device.

In some embodiments, the device may be moved mechanically by an arm of a lubricating apparatus. In some embodiments, the device may be moved by a pressure difference applied thereto.

In some embodiments, the device may be moved in a single direction relative to the surface of the tubular element whilst in contact with the surface of the tubular element.

In some embodiments, the device may be moved in a first direction relative to the surface of the tubular element whilst in contact with the tubular element and in a second direction relative to the tubular element whilst in contact with the tubular element.

In some embodiments, the second direction may be the opposite direction to the first direction.

This may advantageously allow the life cycle of the brush portion to be temporally increased by reducing wear on the leading radial projections by using the life cycle of each end of the brush portion alternately.

In some embodiments, the device may be rotated 180 degrees about an axis perpendicular to its longitudinal axis between movements in the first and second directions.

This may advantageously allow the life cycle of one end of the brush portion to be exhausted before using the other end of the brush portion as the leading end to perform another life cycle.

In some embodiments, the device may be moved at a speed of between about 0.1 m/s to about 1.6 m/s.

In some embodiments, the maximum radial force experienced by a single radial projection or revolution may be in the region of between about 25N to about 60N. In some embodiments, the minimum radial force experienced by a single radial projection or revolution may be in the region of between about 20N to about 40N.

This may give rise to the advantage that sufficient contact force is maintained between the brush portion and the tubular elements being lubricated across the life of the device, which results in a more homogeneous treatment performance by the device throughout its life, and therefore more consistent results.

In some embodiments, the device may comprise a shaft portion which is formed from plastic.

This may give rise to the advantage that the device is lightweight and can be manufactured in an efficient manner with regards to both cost and the environment. That is, the plastic, i.e., thermoplastic elastomer and/or polyolefin, shaft portion provides a lightweight device that is also durable and capable of being easily manufactured by moulding.

In some embodiments, the method may further comprise the step of fabricating the device by moulding the brush portion over the plastic shaft portion.

In some embodiments, the brush portion of the device may comprise a helical form, wherein an outer diameter of the helical form formed by at least one contact zone is tapered at both longitudinal ends of the brush portion such that the outer diameter of the helical form is reduced at the longitudinal ends of the brush portion.

The helical form provides the advantage that the radial projection is more rigid and so able to provide more force against the tubular element for a medicament delivery device to encourage transfer of lubricant agent to the surface. In addition, the helical form provides the advantage of improved homogeneity of the lubricant agent deposit on the surface of the tubular element of a medicament delivery device.

The contact zones being closer to the longitudinal axis of the shaft portion at the longitudinal ends of the brush portion compared to the more central contact zones creates a generally ovoid profile of the brush portion. The ovoid shape of the brush portion reduces the wear on the leading edge of the brush portion and helps to centre the device on entry to a tubular element for a medicament delivery device. This reduces wobble, i.e., the longitudinal axis of the shaft moving about relative to the longitudinal axis of the tubular element for a medicament delivery device. The centring of the device enables more consistent and uniform lubrication of the tubular element for a medicament delivery device by providing a more uniform force profile at the contact zones.

In some embodiments, the brush portion comprises a single helical form, the helical form comprising a single continuous contact zone that is formed by a free end at the outer diameter of the helical form.

This single, rigid contact surface is what provides the improved homogeneity of the lubricant agent deposit on the surface of the tubular element. The single continuous contact surface may be more resistant to bending, thus causing more consistent contact with the inner surface of a tubular element for a medicament delivery device.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which.

DETAILED DESCRIPTION

In many devices, there is a need for components to move relative to each other. In such devices, the components that move relative to each other are often in contact with each other as they move. This gives rise to frictional forces, which oppose the motion of the components relative to each other. In some cases, the frictional forces can be large enough to prevent the proper functioning of the device.

Such a device comprises at least a first component having a first sliding surface and a second component having a second sliding surface in contact with the first sliding surface. For example, the first component may be a tubular housing and the second component may be a component that is moveable within the tubular housing. In some embodiments, the device may be a medicament delivery device.

It is known to use an apparatus, which scrapes or abrades the sliding surfaces of a device in an attempt to smooth the surface, and therefore reduce the frictional force experienced by the components during their relative movement. This is achieved by removing parts of the sliding surface, which deviate most from the average or ideal surface. However, removing material from the components in this way is not precise. Too little or too much material can be removed, which results in surfaces that are still too rough or components with weak points in them that are more likely to fail during use.

The present disclosure is focused on reducing the frictional forces experienced by the sliding surfaces by providing a device for lubricating the sliding surfaces of components during the manufacture of a device, as will be described in more detail hereinafter. By lubricating a sliding surface of a device, the coefficient of friction of the sliding surface can be reduced without removing more material from the component and without the risk of creating weak points in the component.

The device referred to in the application is also known as a lubricating shuttle and the two terms may be used interchangeably throughout the application.

Figure 1:
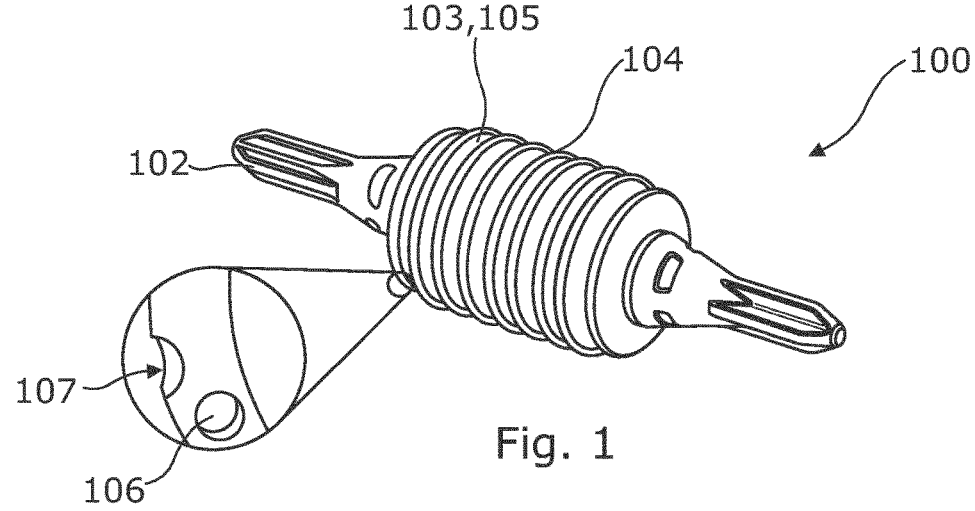
FIG. 1 is a schematic perspective view of a device for lubricating a surface according to the present disclosure.
Figure 2:
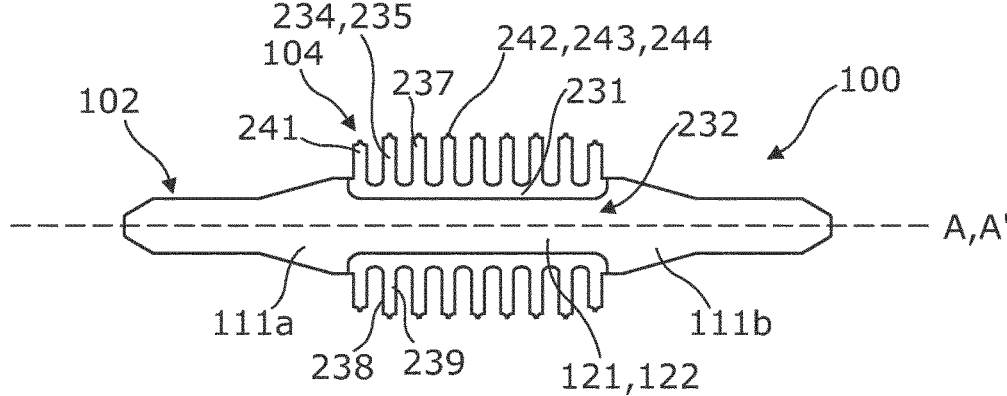
FIG. 2 is a schematic cross-sectional view of the device shown in FIG. 1.

Referring now to FIG. 1 and FIG. 2, a schematic perspective view of an embodiment of a device 100 according to the present disclosure and a schematic cross-sectional view of the embodiment of the device 100 are shown. The device 100 is configured to lubricate a surface, such as, for example, but not limited to, an inner surface of a tubular element for a medicament delivery device. The device 100 comprises a shaft portion 102 having a longitudinal axis A, and a brush portion 103. The brush portion 103 is located on the shaft portion 102. The brush portion 103 comprises at least one contact zone 104 which is configured for contacting an inner surface of a tubular element for a medicament delivery device during use.

In some embodiments, the length of the shaft portion 102 may be in the range of about 50 mm to about 60 mm. In some embodiments, the shaft portion 102 is about 53 mm long. In some embodiments, the length of the brush portion 103 may be in the range of about 16 mm to about 25 mm. In some embodiments, the brush portion 103 is about 19 mm long. In some embodiments, the brush portion 103 may have a diameter in the range of about 10 mm to about 20 mm. In some embodiments, the brush portion 103 may have a diameter of about 13 mm, especially when lubricating a tubular element for a medicament delivery device having a diameter in the range of about 12.5 mm. The shaft portion 102 may be formed from, for example, but not limited to a plastic, such as a thermoplastic elastomer and/or polyolefin.

The brush portion 103 is formed from a brush portion material 105. The brush portion material 105 is impregnated with a lubricant agent 106. The lubricant agent 106 is configured to be transferred from the at least one contact zone 104 to an inner surface of a tubular element for a medicament delivery device during use. The brush portion material 105 provides the structural element of the brush portion 103. The lubricant agent 106 provides a functional element of the brush portion 103.

In the present embodiment, the shaft portion 102 is generally cylindrical in cross-section, although the radius of the shaft portion 102 may vary along its longitudinal axis, and extends through the brush portion 103. That is, the brush portion 103 extends around the shaft portion 102 at long at least a part of the length of the shaft portion 102. The shaft portion 102 may extend through the centre of the brush portion 103, as will be described in more detail hereinafter.

The brush portion material 105 may be formed from a thermoplastic elastomer. The thermoplastic elastomer may be, for example, but not limited to a polyolefin. In some embodiments, the thermoplastic elastomer may be formed from a blend of a plurality of polyolefins. At least one of the polyolefins may be a vulcanized thermoplastic. At least one of the polyolefins may be a non-vulcanized thermoplastic. Example of a polyolefin that may be used to form the brush portion material 105 are ethylene-propylene-diene-monomer and poly-amide. The polyolefin may be reinforce with fibres. Other examples include styrenic thermoplastic with an elastomeric unit such as butadiene, i.e., polystyrene-butadiene-styrene or polystyrene-ethylene-butylene-styrene.

The lubricant agent 106 may be, for example, but not limited to, a siloxane polymer. An example of a siloxane polymer is polydimethylsiloxane (hereinafter referred to as 'PDMS') The thermoplastic elastomer brush portion material 105 may have a Young's modulus of about 2400 MPa. The lubricant agent 106 may have a Young's modulus of about 40 MPa. The thermoplastic elastomer which forms the brush portion material 105 is formed such that it comprises a plurality of pores 107 or spaces. Each of the plurality of pores 107 may receive lubricant agent 106. In this way, the brush portion material 105 is formed in a similar manner to a sponge.

Polydimethylsiloxane (PDMS) is an example of a silicone oil. PDMS is a particularly good example of a lubricant agent 106 because it is optically clear, inert, non-toxic, and non-flammable.

The brush portion 103 is formed by combining the brush portion material 105 with the lubricant agent 106. The brush portion material 105 and lubricant agent 106 may be mixed together to form a substantially uniform mixture. The lubricant agent 106 is provided in a high concentration such that molecules of the lubricant agent only form weak covalent bonds with the brush portion material 105. The mixture is pushed by a screw into a mould in the usual way for injection moulding to achieve the desired shape, as will be discussed hereinafter.

The at least one contact zone 104 may be closer to the longitudinal axis A of the shaft portion 102 at at least one longitudinal end of the brush portion than the at least one contact zone 104 spaced from the end of the brush portion 103 in the longitudinal direction.

The brush portion 103 is configured such that the lubricant agent 106 exudes from the brush portion 103, during use. That is, at least some of the lubricant agent 106 can leave the brush portion material 105 during use to coat an inner surface of a tubular element for a medicament delivery device. Thus, the lubricant agent 106 may be present in spaces between brush portion material 105 of the brush portion 103 in a manner analogous to pores of a sponge. The lubricant agent 106 is interspersed within the structural brush portion material 105 of the brush portion 103 such that the lubricant agent 106 is able to migrate towards the at least one contact zone 104. The coefficient of friction between the device 100 and the inner surface of the tubular element for a medicament delivery device may be about 0.08 as the lubricant agent is transferred.

In the present embodiment, the concentration of lubricant agent 106 able to be received in the brush portion material 105 is in the range of 40% to 60% of the weight of the brush portion 103, before use. An amount of lubricant agent 106 within this range results in a high concentration of, for example, PDMS molecules in the thermoplastic elastomer brush portion material 105. At these high concentrations, not all the PDMS molecules can form a covalent bond with the thermoplastic elastomer brush portion material 105.

That is, despite the plasticisation step associated with the manufacture of the thermoplastic elastomer material 105 that forms the brush portion 103, there are not enough molecules of the thermoplastic elastomer with available electrons to form a covalent bond with each of the PMDS molecules. Thus, the PDMS molecules which are not bonded to the thermoplastic elastomer brush portion material 105 are interspersed within the brush portion material 105. The non-bonded PDMS molecules are able to move within brush portion material 105.

The brush portion material 105 of the brush portion 103 may be compressible in a direction perpendicular to the longitudinal axis of the shaft portion 102 of the device 100. In this context, resiliently compressible means that the brush portion 103 may be compressed when placed under the load of an external force but that once the external force is removed, the brush portion 103 returns to its original shape. In addition, the brush portion material 105 of the brush portion 103 may be resiliently deformable in a direction parallel to the longitudinal axis A of the shaft portion 102 of the device 100. In this context, resiliently deformable means that the brush portion 103 may be deformed when placed under the load of an external force but that once the external force is removed, the brush portion 103 returns to its original shape. Thus, the brush portion material 105 of the brush portion 103 is flexible in a direction parallel to the longitudinal axis A of the shaft portion 102.

This enables the device 100 to be placed inside a tubular element for a medicament delivery device which has an internal cavity with a dimension of its cross-section, i.e., diameter, that is smaller than a cross-sectional dimension, i.e., diameter, of the device 100. Therefore, at least one contact zone 104 will contact an inner surface of a tubular element, during use. The compressibility and/or resilient deformability of the brush portion 103 means that the device 100 can be used to lubricate tubular elements that have a smaller, or significantly smaller, radius than the radius of the device 100.

The PDMS molecules migrate to a surface of the brush portion 103 and are thus in a position to be transferred onto an inner surface of a tubular element for a medicament delivery device, during use. This process is known as exudation. As will be explained in more detail hereinafter, the transfer of the lubricant agent 106 is obtained, in one embodiment, by contact between the brush portion 103 of the device 100 and an inner surface of a tubular element. The transfer of the lubricant agent 106 is assisted by a local temperature elevation, which is due to the brush portion 103 being compressed during use and the increased friction caused by the velocity at which the device 100 is moved relative to a tubular element.

The lubricating device 100 is configured to deposit a layer of lubricant agent 106 on an inner surface of a tubular element for a medicament delivery device. It has been found that the layer of lubricant agent 106 deposited on an inner surface of a tubular element may actually increase the roughness of the surface. It has been found that the increase in surface roughness may be between 10% and 30%. This is due to the lubricant agent 106, for example, PDMS, particles being deposited onto an internal surface of a tubular element. The increase surface roughness is due to the layer of lubricant agent 106 being non-homogenous. That is, the layer of lubricant agent 106 is not uniform in thickness. The layer of lubricant agent 106 may be in the range of about 40 nm to about 60 nm. Therefore, it is clear from the increased surface roughness that lubricant agent 106 is deposited onto a surface from the brush portion 103 rather than the rough surface being scraped smooth, as is claimed in the known art.

Figure 3:
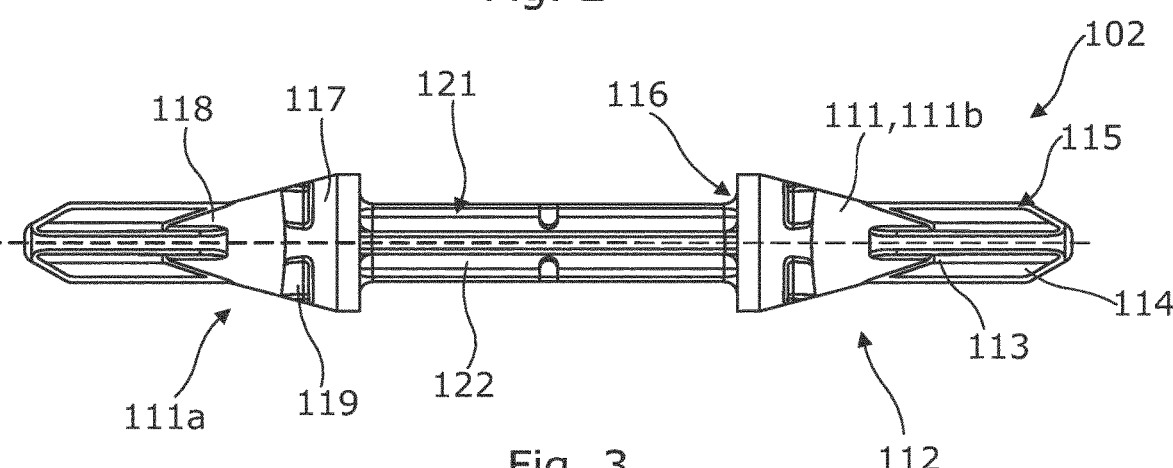
FIG. 3 is a schematic side view of a first embodiment of a shaft portion of a device.

Referring now to FIG. 3, a side view of the shaft portion 102 of the device 100 is shown. The shaft portion 102 comprises a guiding feature 111. The guiding feature 111 is located on an end 112 of the shaft portion 102. That is, the guiding feature 111 forms an extremity 113 of the shaft portion 102 and a section of the shaft portion 102 that extends away from the extremity 113.

The guiding feature 111 comprises an axle portion 114. The axle portion 114 forms the extremity 113 of the shaft portion 102 and extends longitudinally. The axle portion 114 of the guiding feature 111 is configured to allow the device 100 to be gripped by a tool (not shown). The tool may be, for example, but not limited to, an arm of a manufacturing robot (not shown). The axle portion 114 may be configured to be driven through a tubular element for a medicament delivery device to be lubricated, during use.

In some embodiments, as shown in FIG. 3, the axle portion 114 comprises at least one cut-out section 115. The cut-out section 115 improves the grip-ability of the axle portion 114 of the device 100. That is, the at least one cut-out section 115 in the axle portion 114 makes it easier for a tool (not shown) to grip and hold the device 100. In the present embodiment, the axle portion 114 comprises four cut-out sections 115. Each of the cut-out sections 115 has a generally sector shaped cross-section which extends longitudinally. The cut-out sections 115 are evenly spaced circumferentially. Therefore, the axle portion 114 comprises a cross-shaped cross-section extending in the longitudinal direction.

The guiding feature 111 further comprises a surface 116 configured to abut the brush portion 103. The surface 116 extends substantially perpendicularly to the longitudinal axis A of the shaft portion 102. In the present embodiment, the surface 116 of the guiding feature 111 is substantially circular, although it will be understood that in an alternative embodiment, the surface 116 of the guiding feature 111 may be a different shape. The surface 116 is configured to abut the brush portion 103 to prevent longitudinal movement of the brush portion 103 relative to the shaft portion 102 in the direction towards the extremity 113 of the shaft portion 102.

The guiding feature 111 further comprises a tapered section 117. In the present embodiment, the tapered section 117 is a conical section 117. The conical section 117 extends between the axle portion 114 and the surface 116. That is, the conical section 117 comprises the surface 116, which is on the opposite side of the conical section 117 to the axle portion 114. The radius of the surface 116 is greater than the radius of the axle portion 114 such that an apex portion 118 is closer to the extremity 113 of the shaft portion 102 than the surface 116. The apex portion 118 of the conical section 117 blends into the axle portion 114. It will be understood that in alternative embodiments, the tapered section 117 may take the form of another shape, which is based on the cross-sectional shape of the surface 116. That is, the tapered section may generally be pyramidal in shape.

The tapered section 117 provides the surface 116 with the strength to oppose any forces applied to it by the brush portion 103, during use. In addition, the tapered section 117 may comprise at least one cavity 119. The at least one cavity 119 is configured to reduce the weight of the shaft portion 102. The at least one cavity 119 may reduce the weight of the shaft portion 102 without significantly effecting the strength of the tapered section 117.

As shown in FIG. 1 to FIG. 3, the shaft portion 102 of the device 100 comprises a brush portion receiving section 121.

The brush portion receiving section 121 is configured to receive the brush portion 103. The brush portion receiving section 121 extends longitudinally. The brush portion receiving section 121 extends away from the guiding feature 111. That is, the brush portion receiving section 121 projects from the surface 116 and extends away from the surface 116 in the longitudinal direction. The brush portion receiving section 121 may extend from the centre of the surface 116. In some embodiments, the brush portion receiving section 121 is coaxial with the guiding feature 111.

Figures 4, 5, 6, 7, 8, 9, 10, 11:
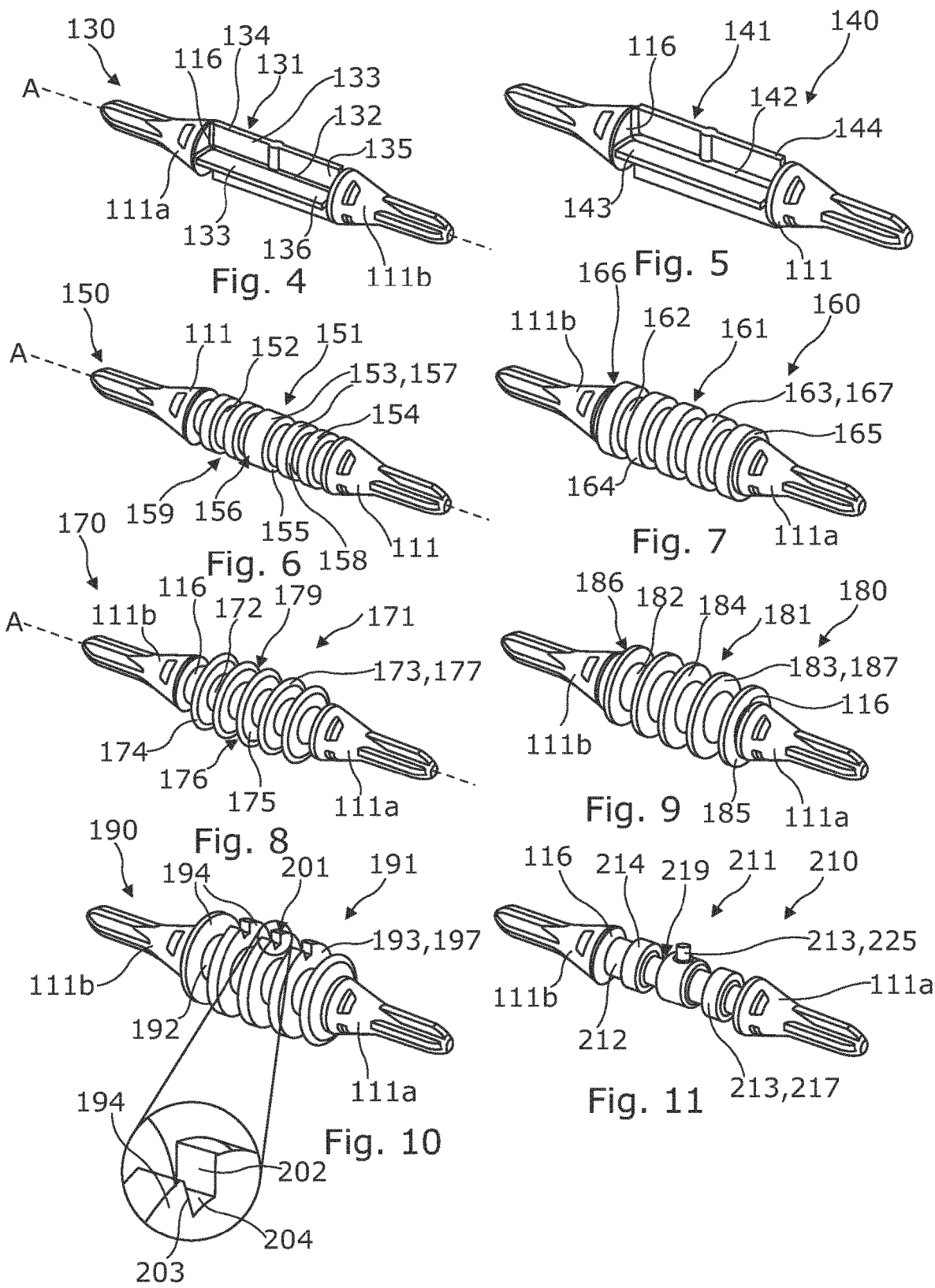
FIG. 4 is a schematic perspective view of a second embodiment of a shaft portion of a device.
FIG. 5 is a schematic perspective view of a third embodiment of a shaft portion of a device.
FIG. 6 is a schematic perspective view of a fourth embodiment of a shaft portion of a device.
FIG. 7 is a schematic perspective view of a fifth embodiment of a shaft portion of a device.
FIG. 8 is a schematic perspective view of a sixth embodiment of a shaft portion of a device.
FIG. 9 is a schematic perspective view of a seventh embodiment of a shaft portion of a device.
FIG. 10 is a schematic perspective view of an eighth embodiment of a shaft portion of a device.
FIG. 11 is a schematic perspective view of a ninth embodiment of a shaft portion of a device.

In the present embodiment, the shaft portion 102 of the device 100 comprises a plurality of guiding features 111. As illustrated in FIG. 3 and FIG. 4, the shaft portion 102 comprises a first guiding feature 111a and a second guiding feature 111b. The first and second guiding features 111a, 111b are spaced apart in the longitudinal direction. Therefore, the first and second guiding features 111a, 111b are spaced apart along the longitudinal axis of the shaft portion 102 and separated by the brush portion receiving section 121. That is, in the present embodiment, the brush portion receiving section 121 is defined or delimited by a guiding feature 111 at each end of the brush portion receiving section 121.

Thus, the first guiding feature 111a is configured to prevent longitudinal movement of the brush portion 103 in a first direction along the longitudinal axis A of the shaft portion 102 relative to the shaft portion 102. The second guiding feature 111b is configured to prevent longitudinal movement of the brush portion in a second opposing direction along the longitudinal axis A relative to the shaft portion 102.

As shown in FIG. 2, the brush portion receiving section 121 comprises a core section 122. The core section 122 extends longitudinally along the length of the brush portion receiving section 121. That is, in the present embodiment, the core section 122 extends the length of the brush portion receiving section 121 between the first guiding feature 111a and the second guiding feature 111b. In the embodiment illustrated in FIG. 4, the core section 122 of the brush portion receiving section 121 is generally circular in cross-section such that the core section 122 is cylindrical.

FIG. 2 shows the brush portion receiving section 121 in its most simplified form, i.e., being formed by a cylindrical core section 122 only. However, referring to FIG. 4 to FIG. 12, nine further exemplary embodiments of the shaft portion 102 of the device 100 are shown, each with an alternative brush portion receiving section. The exemplary embodiments of the shaft portion 102 will be described in more detail hereinafter.

Referring to FIG. 4, there is shown a second embodiment of a shaft portion 130. The shaft portion 130 is generally the same as the embodiment of the shaft portion 102 described above so a detailed description will be omitted herein. Furthermore, features and components of the shaft portion 130 that are the same as features and components of the shaft portion 102 will retain the same terminology and reference numerals. The main difference between the second embodiment of the shaft portion 130 and the previously described shaft portion 102 can be found in a brush portion receiving section 131 of the shaft portion 130.

The shaft portion 130 illustrated in FIG. 4 comprises a brush portion receiving section 131. The brush portion receiving section 131 comprises a core section 132. The core section 132 extends longitudinally along the length of the brush portion receiving section 131 between the guiding features 111a, 111b.

In the present embodiment, the brush portion receiving section 131 further comprises at least one radial projection 133. The at least one radial projection 133 projects radially from the core section 132 of the brush portion receiving section 131. That is, the at least one radial projection 133 projects radially from the core section 132 in a direction perpendicular to the longitudinal axis A of the shaft portion 130.

Although in the present embodiment the core section may comprise a cylinder, in alternative embodiments, the core section 132 may be formed by a square prism having sides with a length equal to the thickness of the at least one radial projection 133.

In addition, the at least one radial projection 133 extends longitudinally along at least a part of the brush portion receiving section 131. That is, the at least one radial projection 133 extends at least partially along the core section 132 between the guiding features 111. In the present embodiment, the at least one radial projection 133 extends in a direction parallel to the longitudinal axis of the shaft portion 130.

Furthermore, the at least one radial projection 133 of the present disclosure extends substantially from the first guiding feature 111a to the second guiding feature 111b of the shaft portion 130. That is, the at least one radial projection 133 extends along the full length of the brush portion receiving section 131. In some embodiments, the at least one radial projection 133 may abut the surface 116 of the guiding features 111.

As shown in FIG. 4, the brush portion receiving section comprises a plurality of radial projections 133. Specifically, in the present embodiment of the brush portion receiving section 131 comprises four radial projections 133. The four radial projections are spaced equally around the core section 132 such that they form a generally cross-shaped cross section, together with the core section 132, when viewed in a plane extending perpendicularly to the longitudinal axis A of the shaft portion 130. Each of the radial projections 133 are cuboidal, having a rectangular cross-section. However, it will be appreciated that in an alternative embodiment the shape of the radial projections 133 may be different.

Each of the radial projections 133 comprises a free end 134. The free end 134 of each radial projections 133 is located at a distance from the centreline of the shaft portion 130, i.e., the longitudinal axis A, equal to the radius of the surface 116 of the guiding feature 111. Therefore, in the present embodiment, the radial projections 133 do not extend beyond the guiding features 111 in the radial direction.

Each of the radial projections 133 also comprise opposing first and second side faces 135, 136 which extend between the core section 132 and the free end 134. The first and second faces 135, 136 abut the brush portion 103 when the brush portion is mounted on the shaft portion 130. In the present embodiment, the first and second faces 135, 136 extend in planes which are parallel to but spaced from each other, and which are parallel to the longitudinal axis A of the shaft portion 130. The first and second faces 135, 136 extend perpendicularly relative to the surface 116 of the guiding feature 111. The first and second faces 135, 136 have a generally rectangular cross-section.

Referring to FIG. 5, there is shown a third embodiment of a shaft portion 140. The shaft portion 140 is generally the same as the embodiment of the shaft portion 130 described above so a detailed description will be omitted herein. Furthermore, features and components of the shaft portion 140 that are the same as features and components of the shaft portion 130 will retain the same terminology and reference numerals. The main difference between the third embodiment of the shaft portion 140 and the previously described shaft portion 130 can be found in the at least one radial projections 143.

The shaft portion 140 illustrated in FIG. 5 comprises a brush portion receiving section 141. The brush portion receiving section 141 comprises a core section 142, as described above. The brush portion receiving section 141 further comprises at least one radial projection 143 extending from the core section 142. In the present embodiment, the brush portion receiving section 141 comprises four radial projections 143, which are evenly spaced around the core section 142.

However, a difference between the third embodiment of the shaft portion 140 shown in FIG. 5 and the second embedment of the shaft portion 130 shown in FIG. 4 is that a free end 144 of the radial projections 143 extends in the radial direction further than the radius of the surface 116 of the guiding features 111. Therefore, the free end 144 of the radial projection 143 is further from the centreline of the shaft portion 140 than the circumference of the surface 116 of the guiding feature 111. The radial projection 143 extending further in the radial direction than the guiding feature 111 increases the available contact area between the brush portion receiving section 141 of the shaft portion 140. Therefore, there is a larger area acting on the brush portion 103, which increases the ability of the shaft portion 140 to prevent movement of the brush portion 103 relative to the shaft portion 140.

Referring now to FIG. 6, there is shown a fourth embodiment of a shaft portion 150. The shaft portion 150 is generally the same as the embodiment of the shaft portion 102 described above so a detailed description will be omitted herein. Furthermore, features and components of the shaft portion 150 that are the same as features and components of the shaft portion 102 will retain the same terminology and reference numerals. The main difference between the fourth embodiment of the shaft portion 150 and those previously described can be found in the at least one radial projection.

The shaft portion 150 illustrated in FIG. 6 comprises a brush portion receiving section 151. The brush portion receiving section 151 comprises a core section 152. The core section 152 extends longitudinally along the length of the brush portion receiving section 151 between the guiding features 111a, 111b.

In the present embodiment, the brush portion receiving section 151 further comprises at least one radial projection 153. The at least one radial projection 153 projects radially from the core section 152 of the brush portion receiving section 151. In the present embodiment, the at least one radial projection 153 projects radially form the core section and in a circumferential direction around the core section 152.

That is, the at least one radial projection 153 comprises a circular disk 157. The circular disk extends perpendicularly to the longitudinal axis A of the shaft portion 150. The perpendicularly extending circular disk 157 is configured to prevent longitudinal movement of the brush portion 103 relative to the shaft portion 150. It will be appreciated that the circular disk 157 could be another shape in a different embodiment, such as a triangular or square plate.

As shown in FIG. 6, the brush portion receiving section 151 comprises a plurality of radial projections 153. Specifically, the present embodiment of the brush portion receiving section 151 comprises five circular disks 157 forming five radial projections 153. Each of the radial projections 153 extends partially along the brush portion receiving section 151 in a direction parallel to the longitudinal axis A of the shaft portion 150.

In the present embodiment, at least one of the radial projections 153, 157 extends along the brush portion receiving section 151 in the longitudinal direction by a distance that is different to the distance that at least one other radial projection 153, 157 extends along the brush portion receiving section 151 in the longitudinal direction. For example, in FIG. 6, the centre disk 157 extends a greater distance in the longitudinal direction along the brush portion receiving section 151 than any of the other radial projections 153, 157, which in this case all extend the same distance in the longitudinal direction.

Each of the plurality of circular disks 157 are spaced apart from each other along the longitudinal axis A of the shaft portion 150. That is, each of the plurality of disks 157 are spaced from one another by a gap 159. The gaps 159 are configured to be filled by the brush portion 103 when the brush portion 103 is mounted on the shaft portion 150, as will be described in more detail hereinafter.

The circular disk 157 comprises a free end 154. The free end 154 of the circular disk 157 is formed by its circumferential surface. The circumferential surface 154 of the at least one radial projection 153 is located at a distance from the centreline of the shaft portion 150 equal to the radius of the surface 116 of the guiding feature 111. Therefore, in the present embodiment, the at least one radial projection 153 does not extend beyond the guiding feature 111 in the radial direction.

Each of the circular disks 157 also comprise first and second side faces 155, 156, which extend between the core section 152 and the circumferential surface 154. Thus an edge 158 is formed where the first and second side faces 155, 156 meet the circumferential surface 154. The first and second faces 155, 156, as well as the circumferential surface 154, are configured to abut the brush portion 103 when the brush portion 103 is mounted on the shaft portion 150. In the present embodiment, the first and second faces 155, 156 extend in planes which are parallel to but spaced from each other, and which are parallel to the surface 116 of the guiding feature 111. The first and second faces 155, 156 extend perpendicularly to the longitudinal axis A of the shaft portion 150.

First and second faces 155, 156 of adjacent circular disks 157 face each other. Therefore, the first face 155 of one disk 157 may be separated from the second face 156 of an adjacent disk 157 by one of the gaps 159. Similarly, the second face 156 of one disk may be separated from the first face 155 of an adjacent disk 157 by one of the gaps 159.

The first and second faces 155, 156 have a generally annular cross-section. In the present embodiment, the first face 155 of the first disk 157 is spaced from the surface 116 of the first guiding feature 111a, and the second face 156 of the last disk 157 is spaced from the surface 116 of the second guiding feature 111b.

Referring now to FIG. 7, there is shown a fifth embodiment of a shaft portion 160. The shaft portion 160 is generally the same as the embodiment of the shaft portion 150 described above so a detailed description will be omitted herein. Furthermore, features and components of the shaft portion 160 that are the same as features and components of the shaft portion 150 will retain the same terminology and reference numerals. The main difference between the fifth embodiment of the shaft portion 160 and the fourth embodiment of the shaft portion 140 can be found in the at least one radial projection.

The shaft portion 160 illustrated in FIG. 7 comprises a brush portion receiving section 161. The brush portion receiving section 161 comprises a core section 162. The core section 162 extends longitudinally along the length of the brush portion receiving section 161 between the guiding features 111*a*, 111*b*.

In the present embodiment, the brush portion receiving section 161 further comprises at least one radial projection 163 in the form of at least one circular disk 167. The at least one circular disk 157 extends perpendicularly to the longitudinal axis of the shaft portion 160. The shaft portion of FIG. 7 comprises five circular disks, which each extend by the same distance along the brush portion receiving section 161 in the longitudinal direction.

In the present embodiment, a free end 164 of the circular disk 167 is located in the radial direction further than the radius of the surface 116 of the guiding features 111. Therefore, the free end 164 (e.g., the circumferential surface 164) of the circular disk 167 is further from the centreline of the shaft portion 160 than the circumference of the surface 116 of the guiding feature 111.

In addition, the first face 165 of the first disk 167 abuts the surface 116 of the first guiding feature 111*a*. That is, there is no gap 169 between the first guiding feature 111*a* and the first disk 167. The second face 166 of the last disk 167 abuts the surface 116 of the second guiding feature 111*b*. That is, there is no gap 169 between the second guiding feature 111*b* and the last disk 167.

Referring now to FIG. 8, there is shown a sixth embodiment of a shaft portion 170. The shaft portion 170 is generally the same as the embodiment of the shaft portion 150 described above so a detailed description will be omitted herein. Furthermore, features and components of the shaft portion 170 that are the same as features and components of the shaft portion 150 will retain the same terminology and reference numerals. The main difference between the sixth embodiment of the shaft portion 170 and the fourth embodiment of the shaft portion 140 can be found in the at least one radial projection.

The shaft portion 170 illustrated in FIG. 8 comprises a brush portion receiving section 171. The brush portion receiving section 171 comprises a core section 172. The core section 172 extends longitudinally along the length of the brush portion receiving section 171 between the guiding features 111*a*, 111*b*.

In the present embodiment, the brush portion receiving section 171 further comprises at least one radial projection 173 in the form of at least one circular disk 177. The at least one circular disk 177 extends perpendicularly to the longitudinal axis of the shaft portion 170. The shaft portion 170 of FIG. 8 comprises five circular disks, which each extend by the same distance along the brush portion receiving section 171 in the longitudinal direction.

In the present embodiment, a free end 174 of the circular disks 177 is located in the radial direction at a distance further than the radius of the surface 116 of the guiding features 111. Therefore, the circumferential surface 174 of the circular disk 177 is further from the centreline of the shaft portion 170 than the circumference of the surface 116 of the guiding feature 111.

Each of the circular disks 177 also comprise first and second side faces 175, 176, which extend between the core section 172 and the circumferential surface 174. In the present embodiment, instead of the circumferential surface 174 being formed by a cylindrical surface as in the previously described shaft portions 150, 160, the circumferential surface 174 is rounded. That is, the circumferential surface 174 which joins a radially outward end of the first face 175 to a radially outward end of the second face 176 is generally dome shaped. The removal of the sharp edge reduces wear on the brush portion 103 during use.

The first and second faces 175, 176, as well as the domed circumferential surface 174, are configured to abut the brush portion 103 when the brush portion 103 is mounted on the shaft portion 170. In the present embodiment, the first and second faces 175, 176 extend in planes which are parallel to but spaced from each other, and which are parallel to the surface 116 of the guiding feature 111. The first and second faces 175, 176 extend perpendicularly to the longitudinal axis A of the shaft portion 170.

First and second faces 175, 176 of adjacent circular disks 177 face each other. Therefore, the first face 175 of one disk 177 may be separated from the second face 176 of an adjacent disk 177 by one of the gaps 179. Similarly, the second face 176 of one disk may be separated from the first face 175 of an adjacent disk 177 by one of the gaps 179.

The first and second faces 175, 176 have a generally annular cross-section. In the present embodiment, the first face 175 of the first disk 177 is spaced from the surface 116 of the first guiding feature 111*a*, and the second face 176 of the last disk 177 is spaced from the surface 116 of the second guiding feature 111*b*.

Referring now to FIG. 9, there is a seventh embodiment of a shaft portion 180. The shaft portion 180 is generally the same as the embodiment of the shaft portion 180 described above so a detailed description will be omitted herein. Furthermore, features and components of the shaft portion 180 that are the same as features and components of the shaft portion 170 will retain the same terminology and reference numerals. The main difference between the seventh embodiment of the shaft portion 180 and the sixth embodiment of the shaft portion 170 can be found in the at least one radial projection.

The shaft portion 180 illustrated in FIG. 9 comprises a brush portion receiving section 181. The brush portion receiving section 181 comprises a core section 182. The core section 182 extends longitudinally along the length of the brush portion receiving section 181 between the guiding features 111*a*, 111*b*.

In the present embodiment, the brush portion receiving section 181 further comprises at least one radial projection 183 in the form of at least one circular disk 187. The at least one circular disk 187 extends perpendicularly to the longitudinal axis of the shaft portion 180. The shaft portion of FIG. 9 comprises five circular disks, which each extend by the same distance along the brush portion receiving section 181 in the longitudinal direction.

In the present embodiment, a free end 184 of the circular disk 187 is located in the radial direction further than the radius of the surface 116 of the guiding features 111. Therefore, the free end 184 (e.g., the circumferential surface 184) of the circular disk 187 is further from the centreline of the shaft portion 180 than the circumference of the surface 116 of the guiding feature 111. The circumferential surface 184 of the shaft portion 180 is domed, as previously described in relation to the embodiment illustrated in FIG. 10.

In addition, the first face 185 of the first disk 187 abuts the surface 116 of the first guiding feature 111*a*. That is, there is no gap 189 between the first guiding feature 111*a* and the first disk 187. The second face 186 of the last disk 187 abuts the surface 116 of the second guiding feature 111*b*. That is, there is no gap 189 between the second guiding feature 111*b* and the last disk 187.

Referring now to FIG. 10, there is shown an eighth embodiment of a shaft portion 190. The shaft portion 190 is generally the same as the embodiments of the shaft portions described above so a detailed description will be omitted herein. Furthermore, the features and components of the shaft portion 190 that are the same as features and components of the shaft portion 190 will retain the same terminology and reference numerals. The main difference between the eighth embodiment of the shaft portion 190 and the other embodiments of the shaft portion described above can be found in the at least one radial projection.

The shaft portion 190 illustrated in FIG. 10 comprises a brush portion receiving section 191. The brush portion receiving section 191 comprises a core section 192. The core section 192 extends longitudinally along the length of the brush portion receiving section 191 between the guiding features 111*a*, 111*b*.

In the present embodiment, the brush portion receiving section 191 further comprises at least one radial projection 193 in the form of at least one circular disk 197. The at least one circular disk 197 extends perpendicularly to the longitudinal axis of the shaft portion 190. The shaft portion of FIG. 10 comprises five circular disks, which each extend by the same distance along the brush portion receiving section 191 in the longitudinal direction.

In the present embodiment, the free end 184 of each of the circular disks 187 is located in the radial direction further than the radius of the surface 116 of the guiding features 111. However, in the present embodiment, the first and last circular disks 197, i.e., the disks 197 closest to the guiding features 111*a*, 111*b*, have a domed circumferential surface 194, similar to the circumferential surface described in relation to FIG. 8. The remaining disks 197, i.e., the disks 197 located between the first and last disks 197, comprising a cylindrical circumferential surface 194, similar to the circumferential surface described in relation to FIG. 6.

The radius of at least one of the plurality of circular disks 197 may be different to the radius of at least another one of the plurality of circular disks 197. For example, as shown in FIG. 10, the first and last circular disks 197 have a smaller radius than the remaining circular disks 197. Although disks 197 of different radii are only illustrated in FIG. 10, it will be understood that any embodiment described herein could additionally comprise circular disks 197 having different sized radii.

Furthermore, at least one of the radial projections 193, for example a circular disk 197, may further comprise a cut-out section 201. The cut-out section 201 is configured to receive a part of the brush portion 103 when the brush portion 103 is located on the shaft portion 190. The cut-out section 201 is configured to prevent rotation of the brush portion 103 relative to the shaft portion 190 by providing an anchor point in the shaft portion 190 through which the brush portion 103 extends.

The cut-out 201 is formed by a recess extending from the free end 194 of the at least one projection 193. In this case, the recess extends from the circumferential surface 194 of the at least one circular disk 197. The recess extends from the free end or circumferential surface 194 radially inwardly towards the core section 192. Therefore, the cut-out comprises first and second side walls 202, 203, which extend radially. The first and second side walls 202 may be joined by a bottom wall 204 of the cut-out 201. The bottom wall 204 may be formed by a curved surface or a planar surface.

It will be appreciated that in an alternative embodiment, the first and second side walls 202, 203 may not extend radially but instead may extend parallel but space from one another. However, in such an embodiment, a centreline of the cut-out 201 may still extend generally radially towards the longitudinal axis of the shaft portion 190.

Referring now to FIG. 11, there is shown a ninth embodiment of a shaft portion 210. The shaft portion 210 is generally the same as the embodiment of the shaft portion 150 described above so a detailed description will be omitted herein. Furthermore, features and components of the shaft portion 150 that are the same as features and components of the shaft portion 150 will retain the same terminology and reference numerals. The main difference between the ninth embodiment of the shaft portion 210 and the previous embodiments of the shaft portion can be found in the at least one radial projection.

The shaft portion 210 illustrated in FIG. 11 comprises a brush portion receiving section 211. The brush portion receiving section 211 comprises a core section 212. The core section 212 extends longitudinally along the length of the brush portion receiving section 211 between the guiding features 111*a*, 111*b*.

In the present embodiment, the brush portion receiving section 211 further comprises at least one radial projection 213 in the form of at least one circular disk 217. The at least one circular disk 217 extends perpendicularly to the longitudinal axis of the shaft portion 210. The shaft portion of FIG. 11 comprises three circular disks.

Each of the three circular disks 217 are spaced apart from each other along the longitudinal axis A of the shaft portion 210. That is, each of the plurality of disks 217 are spaced from one another by a gap 218. In the present embodiment, the middle circular disk 217 extends along the brush portion receiving section 211 in the longitudinal direction by a distance that is different to the distance that the first and last circular disk 217 extend in the longitudinal direction. As illustrated in FIG. 11, the middle circular disk 217 extends further in the longitudinal direction than the first and last circular disks 217.

The circular disk 217 comprises a free end 214. The free end 214 of the circular disk 217 is formed by its circumferential surface. The circumferential surface 214 of the at least one circular disk 217 is located at a distance from the centreline of the shaft portion 210 is less than the radius of the surface 116 of the guiding feature 111. Therefore, it the present embodiment, the circumference of the surface 116 of the guiding feature 111 extends beyond the circumferential surface 214 of the circular disk 217.

Furthermore, the at least one radial projection 213 may comprise a pin 225. The pin 225 may extend radially from the core section 212. Alternatively, as shown in FIG. 11, the pin 225 may extend radially from the circumferential surface 214 of at least one of the circular disks 217. In the present embodiment, the pin 225 is generally cylindrical with a central axis extending perpendicularly to the longitudinal axis A of the shaft portion 210. In an alternative embodiment, the pin 225 may be another shape. The pin may extend so that its free end 226 does not extend beyond the circumference of the surface 116 of the guiding feature 111.

It will be understood that the features and components described above in relation to the embodiments of the shaft portion are only given as examples, and that the features described may be combined in ways not illustrated in the Figures.

Referring back to FIG. 1 and FIG. 2, the first embodiment of the brush portion 103 is shown. The brush portion 103 has a longitudinal axis A'. The longitudinal axis A' of the brush portion is coaxial with the longitudinal axis A of the shaft portion 102. The brush portion 103 comprises a core section 231. The core section 231 of the brush portion 103 extends longitudinally across the brush portion receiving section 121 of the shaft portion 102 between the guiding features 111. The core section 231 comprises a central aperture 232. The shaft portion 102 of the device 100 extends through the central aperture 232. The central aperture 232 comprises an internal surface 233. The internal surface 233 of the brush 103 is configured to abut the brush portion receiving section 121 of the shaft portion 102.

The brush portion 103 may be over-moulded onto the shaft portion 102. Alternatively, the brush portion 103 and shaft portion 102 may be co-moulded. Therefore, the internal surface 233 of the brush portion 103 may contact the brush portion receiving section 121 along its length between the guiding features no matter which components are located on the brush portion receiving section 121 as described in the examples illustrated in FIG. 4 to FIG. 11. That is, the whole of the internal surface may abut the brush portion receiving section 103, and any radial projections, as described above.

The core section 231 may be generally cylindrical and extend about the core section 122 of the brush portion receiving section 121 of the shaft portion 102. The core section 231 of the brush portion 103 may be considered to be the part of the brush portion 103 which is radially inward of the guiding features 111 of the shaft portion 102 or the free end 134 of the radial projection 133 of the brush portion receiving section 121 of the shaft portion 102, whichever is the furthest form the longitudinal axis A of the shaft portion 102, when the brush portion 103 is mounted on the shaft portion 102. In some embodiments, the core section 231 may comprise at least one aperture. The at least one aperture may be configured to allow a radial projection of the shaft portion to extend therethrough.

The brush portion 103 further comprises at least one radial projection 234. The at least one radial projection 234 extends from the core section 231 of the brush portion 103. That is, the at least one radial projection 234 projects radially from the core section 231 in a direction perpendicular to the longitudinal axis A of the shaft portion 102. In addition, the at least one radial projection 234 extends longitudinally along at least a part of the core section 231.

Although in the present embodiment the core section 231 may be generally cylindrical, in alternative embodiments the core section 231 may be formed by, for example, but not limited to, a polygonal prism, i.e., a polyhedron comprising a n-sided polygon base. In further alternative embodiments, the core section 231 may be formed by elements, which are connected between radial projection or by longitudinally extending members, as will be explained in more detail hereinafter.

In the present embodiment, the at least one radial projection 234 is formed by at least one circular disk 235. The at least one circular disk 235 extends in a direction perpendicular to the longitudinal axis A of the shaft portion 102. The perpendicularly extending disk 235 is configured to contact a surface of a tubular element for a medicament delivery device during use. The disk 235 may be dimensioned such that it is resiliently compressible and/or resiliently deformable, during use, as discussed above. It will be appreciated that the circular disk 235 could be another shape in a different embodiment, such as triangular or square. In general, the shape of the disk 235 will be configured to match the inner surface of the tubular element to be lubricated. The radius of the circular disk 235 is configured such that it forms an interference fit with the surface of the tubular element to be lubricated.

As shown in FIG. 2, the brush portion comprises a plurality of radial projections 234 in the form of circular disks 235. Specifically, the present embodiment of the brush portion 103 comprises nine circular disks 235. Each of the circular disks 235 extend partially along the core section 231 in a direction a parallel to the longitudinal axis A'.

In the present embodiment, each of the circular disks 235 extend along the core section 231 in the longitudinal direction by the same distance, although in alternative embodiments the thickness of at least one circular disk may be different to the thickness of another one of the disks 235. In the present embodiment, the circular disks 235 are solid. However, in an alternative embodiment, the circular disks 235 may be hollow.

Each of the plurality of circular disks 235 are spaced apart from each other along the longitudinal axis A of the brush portion 103. That is, each of the plurality of disks 235 are spaced from one another by a gap 236. The gaps 236 are configured to allow the disks 235 the space to bend into, during use.

Each circular disk 235 comprises a free end 237. The free end 237 of the circular disk 235 is formed by its circumferential surface. The circumferential surface 237 of the circular disk 235 is located at a distance from the centreline of the shaft portion 102 greater than the distance from the centreline of the shaft portion to the circumferential surface of the guiding features 111 and brush receiving portion 121. This ensures that it is the brush portion 103 that contacts a surface of a tubular element for a medicament delivery device to be lubricated instead of the shaft portion 102.

Each of the circular disks 235 also comprises first and second faces 238, 239, which extend between the core section 231 of the brush portion 103 and its circumferential surface 237. The circumferential surface 237 is generally domed shaped, as shown in FIG. 2. In the present embodiment, the first and second faces 238, 239 extend in planes which are parallel to but spaced from each other, and which are perpendicular to the longitudinal axis A' of the brush portion 103. In an alternative embodiment, the planes in which the first and second faces 238, 239 extend may be angled relative to each other.

The at least one radial projection 234 comprises at least one contact zone 104. The at least one contact zone 104 is located at an end 241 of the radial projection 234, which is located distally from the core section 231 of the brush portion 103. The end 241 of the radial projection 234 may be formed by the circumferential surface 237. The at least one contact zone 104 comprises at least one contact point 242. The at least one contact point 242 is configured to contact a surface of a tubular element for a medicament delivery device to transfer lubricant agent 106 in the brush portion material 105 to the surface.

As shown in FIG. 2, the contact zone 104 may comprise a single contact point 242. The contact point 242 may be formed by the distal most portion or extremity 243 of the radial projection 234 from the core section 231 of the brush portion 103 in a direction perpendicular to the longitudinal axis A of the shaft portion 102.

In the present embodiment, the contact points 242 of the radial projections 234 are spaced from the longitudinal axis A' of the brush portion 103 by varying distances. For example, the radial projections 234 closest to the ends of the brush portion 103, i.e., proximal to the guiding features, may be shorter in the radial direction than the other radial projections 234. That is, the distance between the longitudinal axis A' and the contact point 242 of the first and last radial projection 234 may be shorter than the distance between the longitudinal axis A' and the contact point 242 of any other radial projections 234. The shape created by the contact points 242 of the contact zones 104 is generally an ovoid. Such an arrangement helps guide the device 100 into the tubular element for a medicament delivery device to be lubricated and properly places the device 100 in the tubular element to provide optimum contact for the transfer of lubricant agent 106 from the brush portion material 105 to the inner surface of the tubular element.

Figures 21, 22, 23A, 23B, 23C:
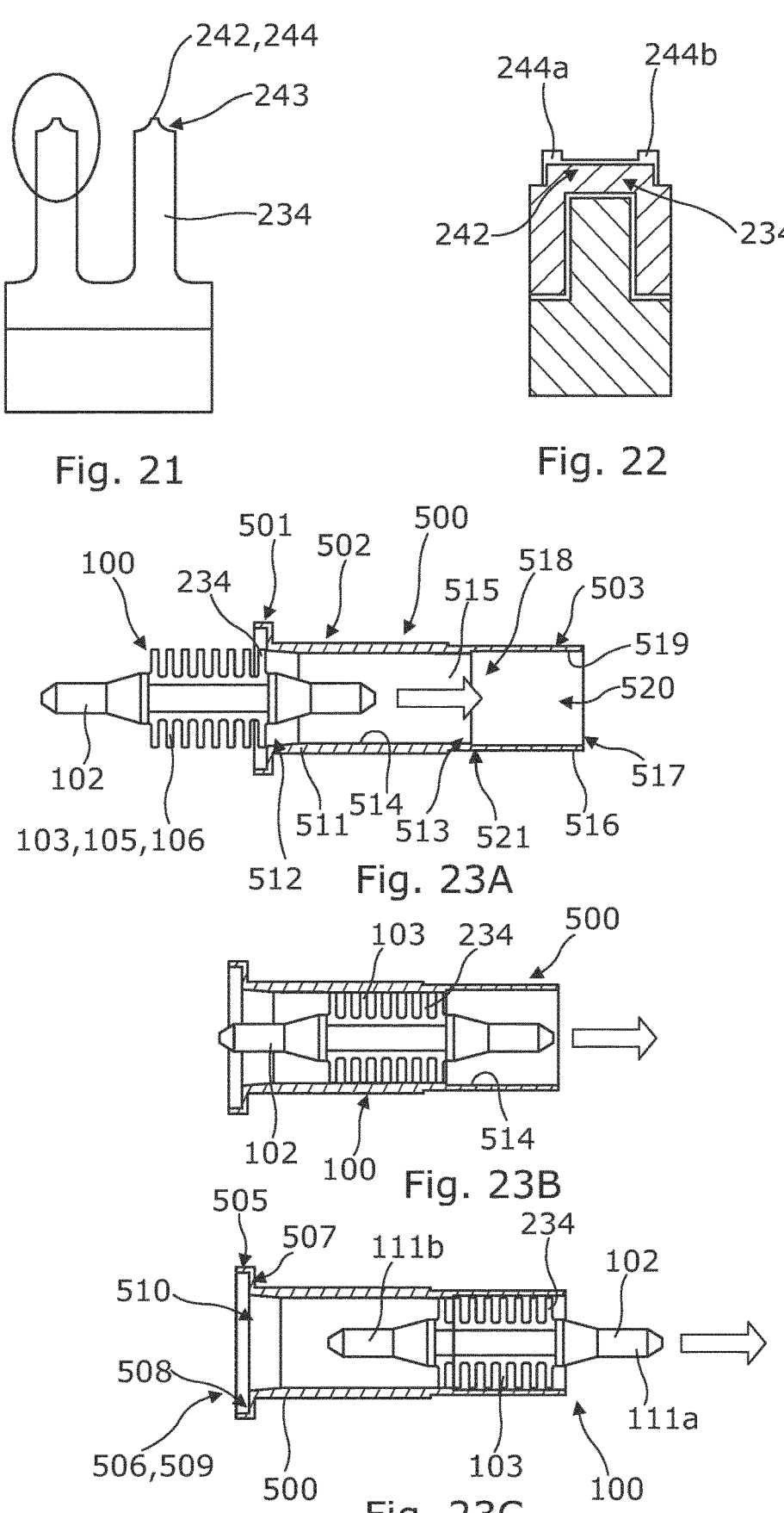
FIG. 21 is an enlarged schematic side view of a brush portion.
FIG. 22 is an enlarged schematic side view of a brush portion.
FIG. 23A is a schematic cross-sectional side view of a device in a first position relative to a component to be lubricated.
FIG. 23B is a schematic cross-sectional side view of a device in a second position relative to a component to be lubricated.
FIG. 23C is a schematic cross-sectional side view of a device in a third position relative to a component to be lubricated.

Referring briefly to FIG. 21 and FIG. 22, the contact point 242 may be formed by at least one lip 244. The at least one lip 244 is formed on the extremity 243 of the radial projection 234. The lip 244 may be formed by, for example, but not limited to, a dome shaped projection. The embodiment of the radial projection 234 in FIG. 21 comprises a single lip 244. The lip 244 may be located centrally on the end 243 of the radial projection 234. This enables the lip 244 to contact a surface of a tubular element for a medicament delivery device no matter which direction the device 100 is moved.

In an alternative embodiment illustrated in FIG. 22, the radial projection 234 may comprise a plurality of lips 244. In the present embodiment, the radial projection 234 comprises two lips 244a, 244b, which are offset from the centreline of the radial projection 234. Therefore, at least one of the two lips 244a, 244b contacts a surface of the tubular element for a medicament delivery device during use. For example, the first lip 244a may contact a surface of a tubular element when the device 100 is moved in one direction and the second lip 244b may contact the surface of a tubular element when the device 100 is moved in the opposite direction.

For instance, the distance between adjacent radial projections 234 in the longitudinal direction may be in the range of about 1.8 mm to about 2.2 mm. Furthermore, the at least one radial projection 234 may have an aspect ratio in the range of about 9 to about 17. The aspect ratio of the at least one radial projection 234 is to be considered to be the ratio of the length of the radial projection 234 in the radial direction from the central longitudinal axis, to the thickness of the radial projection 234 in the longitudinal direction.

Figures 12, 13, 14, 15, 16, 17, 18:
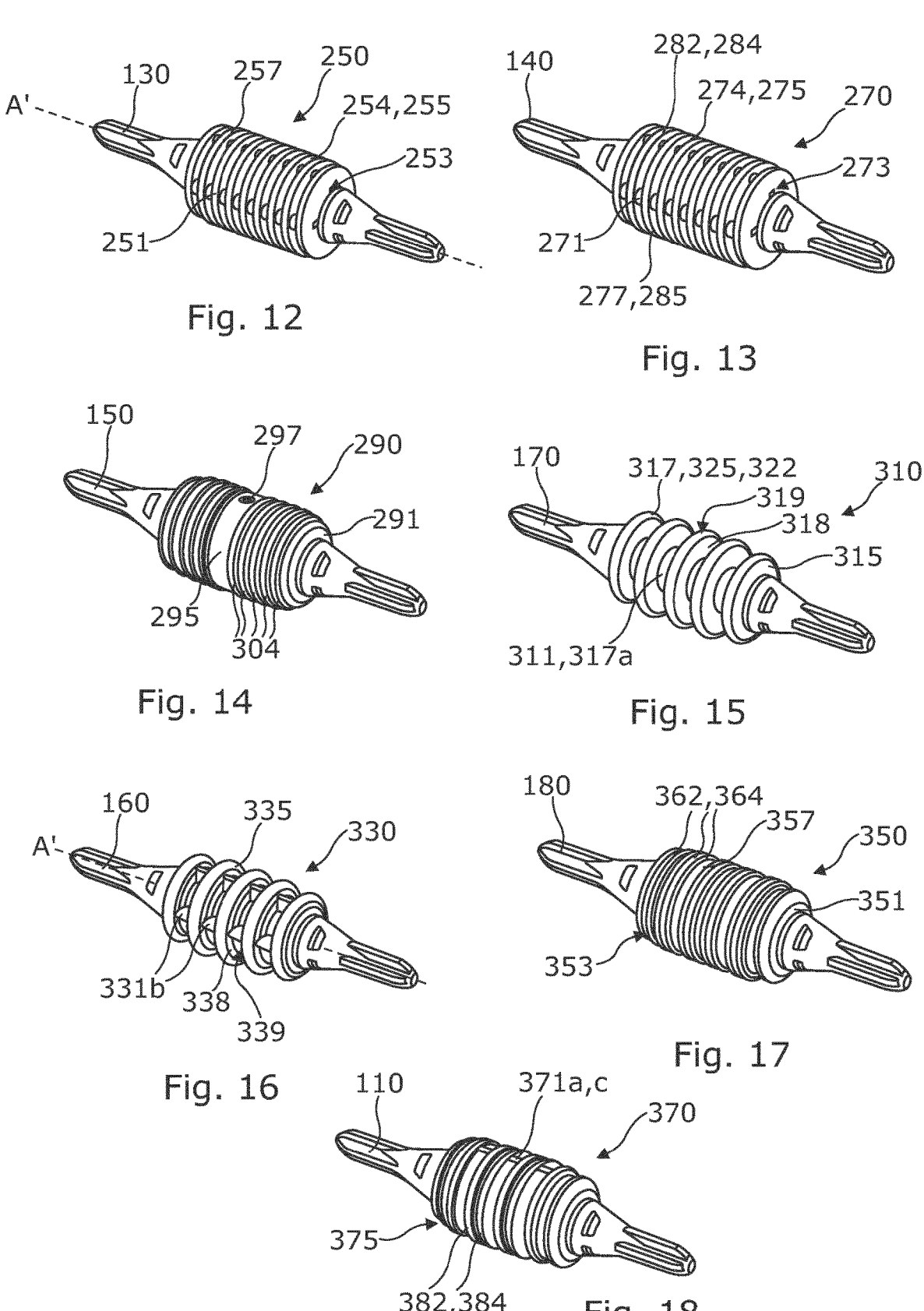
FIG. 12 is a schematic perspective view of a second embodiment of a brush portion of a device.
FIG. 13 is a schematic perspective view of a third embodiment of a brush portion of a device.
FIG. 14 is a schematic perspective view of a fourth embodiment of a brush portion of a device.
FIG. 15 is a schematic perspective view of a fifth embodiment of a brush portion of a device.
FIG. 16 is a schematic perspective view of a sixth embodiment of a brush portion of a device.
FIG. 17 is a schematic perspective view of a seventh embodiment of a brush portion of a device.
FIG. 18 is a schematic perspective view of an eighth embodiment of a brush portion of a device.

Referring now briefly to FIG. 12, there is shown a second embodiment of the brush portion 250. The brush portion 250 is generally the same as the embodiment of the brush portion 103 described above so a detailed description will be omitted herein. Furthermore, features and components of the brush portion 250 that are the same as features and components of the brush portion 103 will retain the same terminology and reference numerals.

FIG. 12 shows a brush portion 250 mounted on a shaft portion 130 similar to that illustrated in FIG. 4. However, it will be understood that in other embodiments, the brush portion 250 may be located on a different shaft portion by moulding the brush portion over a different shaft portion.

In the present embodiment, the brush portion 250 comprises a core section 251, which has a cross-shaped cross section. That is, the core section 251 of the brush portion 250 extends around the cross-shaped brush portion receiving section 131 of the shaft portion 130 such that the entire surface of the brush portion receiving section 131 abuts the inner surface 253 of the brush portion 250. The cross-shaped core section 251 of the brush portion 250 also helps to make the brush portion more rigid to allow good contact between the brush portion 250 and a surface to be lubricated.

The brush portion 250 further comprises at least one radial projection 254. In the present embodiment, the brush portion 250 comprises nine circular disks 255 extending from the core section 251, which form the radial projections 254. Each of the circular disks 255 comprise a circumferential surface 257 which is formed by a domed surface. Thus, the contact point 262 of the circular disks 255 is formed by the apex 265 of the dome.

In the present embodiment, at least one of the circular disks 255 extends at a different distance from the longitudinal axis A' of the brush portion 250 to at least one of the other circular disks 255. Therefore, there may be at least two circular disks 255 that have different aspect ratios. The circular disks 255 which are not at the ends of the brush portion 103 may have the same aspect ratio.

Referring now briefly to FIG. 13, there is shown a third embodiment of the brush portion 270. The brush portion 270 is generally the same as the embodiment of the brush portion 250 described above so a detailed description will be omitted herein. Furthermore, features and components of the brush portion 270 that are the same as features and components of the brush portion 250 will retain the same terminology and reference numerals.

FIG. 13 shows a brush portion 270 mounted on a shaft portion 140 similar to that illustrated in FIG. 5. However, it will be understood that in other embodiments, the brush portion 270 may be located on a different shaft portion by moulding the brush portion over a different shaft portion.

In the present embodiment, the brush portion 270 comprises a core section 271, which has a cross-shaped cross section. That is, the core section 271 of the brush portion 270 extends around the cross-shaped brush portion receiving section 141 of the shaft portion 140 such that the entire surface of the brush portion receiving section 11 abuts the inner surface 273 of the brush portion 270. The cross-shaped core section 271 of the brush portion 270 also helps to make the brush portion more rigid to allow good contact between the brush portion 270 and a surface to be lubricated.

The brush portion 270 further comprises at least one radial projection 274. In the present embodiment, the brush portion 270 comprises nine circular disks 275 extending from the core section 271, which form the radial projections 274. Each of the circular disks 275 comprise a circumferential surface 277, which is formed by a domed surface. The circumferential surface 277 further comprises a lip 284 projecting from the apex 285 of the dome. Thus, the contact point 282 of the circular disks 275 is formed by the circumferentially extending lip 284.

In the present embodiment, at least one of the circular disks 275 extends at a different distance from the longitudinal axis A' of the brush portion 270. The circular disks of the third embodiment of the brush portion 270 are longer, in the radial direction, than the circular disks of the second embodiment of the brush portion 250.

Referring now briefly to FIG. 14, there is shown a fourth embodiment of the brush portion 290. The brush portion 290 is generally the same as the embodiment of the brush portion 103 described above so a detailed description will be omitted herein. Furthermore, features and components of the brush portion 290 that are the same as features and components of the brush portion 103 will retain the same terminology and reference numerals.

FIG. 14 shows a brush portion 290 mounted on a shaft portion 150 similar to that illustrated in FIG. 6. However, it will be understood that in other embodiments, the brush portion 290 may be located on a different shaft portion by moulding the brush portion over a different shaft portion.

In the present embodiment, the brush portion 290 comprises a cylindrical core section 291, which abuts the whole surface of the brush portion receiving section 151. Furthermore, the brush portion 290 comprises a single circular disk 295, which extends the length of the brush portion receiving section 151 between the guiding features 111. The circumferential surface 297 of the circular disk 295 is formed by a cylindrical surface. The cylindrical circumferential surface 297 comprises ten lips 304 arranged to form multiple contact points 302. The ten lips 304 are arranged such that a first group of five of the lips 304 are located proximal one end of the brush portion 290 and a second group of five lips 304 are located proximate the other end of the brush portion 290. At least one of the lips 304 closest to an end of the brush portion 290 has a contact point 302 that is closer to the longitudinal axis A of the shaft portion 150 than another one of the lips 304. In the present embodiment, the first and second groups of lips 304 are separated by a distance d. However, it will be understood that in other embodiments, alternative arrangements are envisaged.

Referring now briefly to FIG. 15, there is shown a fifth embodiment of the brush portion 310. The brush portion 310 is generally the same as the embodiment of the brush portion 103 described above so a detailed description will be omitted herein. Furthermore, features and components of the brush portion 310 that are the same as features and components of the brush portion 103 will retain the same terminology and reference numerals.

FIG. 15 shows a brush portion 310 mounted on a shaft portion 170 similar to that illustrated in FIG. 8. However, it will be understood that in other embodiments, the brush portion 310 may be located on a different shaft portion by moulding the brush portion over a different shaft portion.

The brush portion 310 comprises a core section 311, which extends longitudinally across the brush portion receiving section 171 of the shaft portion 170. The core section 311 comprises a plurality of apertures therein, which are configured to allow the disks 313 of the shaft portion 170 to extend therethrough. Thus, the core section 311 is formed by a plurality of cylindrical parts 311*a*. The cylindrical parts 311*a* of the core section 311 have an inner surface 313 which abuts the core section 172 of the brush portion receiving section 171 of the shaft portion 170. The parts of the core section 311 are joined together by the circular disks 315, which extend over the disks 173 of the shaft portion. Thus, in the present embodiment, the core section 311 is not continuous. However, the inner surface 313 of the brush portion 310 still contacts the whole of the surface of the brush portion receiving section 171 of the shaft portion 170.

In the present embodiment, the brush portion 310 comprises five circular disks 315 which each extend over a disk 177 of the shaft portion 170. Each of the plurality of circular disks 315 are spaced apart from each other along the longitudinal axis A of the brush portion 310. Each circular disk 315 comprises a free end 317. The free end 317 of the circular disk 315 is formed by its circumferential surface. Each of the circular disks 315 also comprises first and second faces 318, 319, which extend between the core section 311 of the brush portion 310 and its circumferential surface 317. The circumferential surface 317 is generally domed shaped and so the apex 325 of the dome forms the contact point 322. At least one of the disks 315 closest to an end of the brush portion 310 has a contact point 322 that is closer to the longitudinal axis A of the shaft portion 170 than another one of the contact points 322.

Referring now briefly to FIG. 16, there is shown a sixth embodiment of the brush portion 330. The brush portion 330 is generally the same as the embodiment of the brush portion 310 described above so a detailed description will be omitted herein. Furthermore, features and components of the brush portion 330 that are the same as features and components of the brush portion 310 will retain the same terminology and reference numerals.

FIG. 16 shows a brush portion 330 mounted on a shaft portion 160 similar to that illustrated in FIG. 7. However, it will be understood that in other embodiments, the brush portion 330 may be located on a different shaft portion by moulding the brush portion over a different shaft portion.

In the present embodiment, the core section 331 is not formed by cylindrical parts which surround and contact the core section 162 of the brush portion receiving section 161 of the shaft portion 160. Instead, in the present embodiment, the core section is formed of a plurality of radially projecting elements 331*b*, which extend in the longitudinal direction between the adjacent circular disks 335. That is, an element 331*a* extends from the first face 338 of one circular disk 335 to the second face 339 of an adjacent circular disk 335. In the present embodiment, four radial elements 331*a* extend between each pair of adjacent circular disks 335. The radial elements 331*a* are spaced evenly about the longitudinal axis A' of the brush portion 330.

Referring now briefly to FIG. 17, there is shown a seventh embodiment of the brush portion 350. The brush portion 350 is generally the same as the embodiment of the brush portion 290 described above so a detailed description will be omitted herein. Furthermore, features and components of the brush portion 350 that are the same as features and components of the brush portion 290 will retain the same terminology and reference numerals.

FIG. 17 shows a brush portion 350 mounted on a shaft portion 180 similar to that illustrated in FIG. 9. However, it will be understood that in other embodiments, the brush portion 350 may be located on a different shaft portion by moulding the brush portion over a different shaft portion.

In the present embodiment, the brush portion 350 comprises a cylindrical core section 351, which abuts the whole surface of the brush portion receiving section 181. Furthermore, the brush portion 350 comprises a single circular disk 355, which extends the length of the brush portion receiving section 181 between the guiding features 111. The circumferential surface 357 of the circular disk 355 is formed by a cylindrical surface.

The cylindrical circumferential surface 357 comprises ten lips 364 arranged to form multiple contact points 362. The ten lips 364 are arranged such that a lip 364 extends circumferentially at points adjacent to the planes in which the first and second faces 185, 186 of the projections 183 extend. Therefore, in the distance between two adjacent projections 183 of the shaft portion 180, two lips 364 extend circumferentially. At least one of the lips 364 closest to an end of the brush portion 350 has a contact point 362 that is closer to the longitudinal axis A of the shaft portion 180 than another one of the lips 364.

Referring now briefly to FIG. 18, there is shown an eighth embodiment of the brush portion 370. The brush portion 370 is generally the same as the embodiment of the brush portion 103 described above so a detailed description will be omitted herein. Furthermore, features and components of the brush portion 370 that are the same as features and components of the brush portion 103 will retain the same terminology and reference numerals.

FIG. 18 shows a brush portion 370 mounted on a shaft portion 190 similar to that illustrated in FIG. 10. However, it will be understood that in other embodiments, the brush portion 370 may be located on a different shaft portion by moulding the brush portion over a different shaft portion.

In the present embodiment, the brush portion 370 comprises a core section 371 formed by plurality of cylindrical parts 371a, which are joined by longitudinally extending elements 371c. The longitudinally extending elements 371c extend through a cut-out section 201 in the radial projections 193 of the shaft portion 190.

A circular disk 375 extends from each of the parts 371a of core section 371. Each of the circular disks 375 comprise two circumferentially extending lips 384, which form a plurality of contact points 384 of the brush portion 370. The embodiment illustrated in FIG. 18 has four circular disks 375 and eight contact points 382. The circular disks 375 at the longitudinal ends of the brush portion 370 may have a smaller radius that the more central circular disks, as described above in relation to previous embodiments. In addition, at least one of the lips 384 closest to an end of the brush portion 370 has a contact point 382 that is closer to the longitudinal axis A of the shaft portion 150 than another one of the lips 304.

Figures 19A, 19B, 19C, 20:
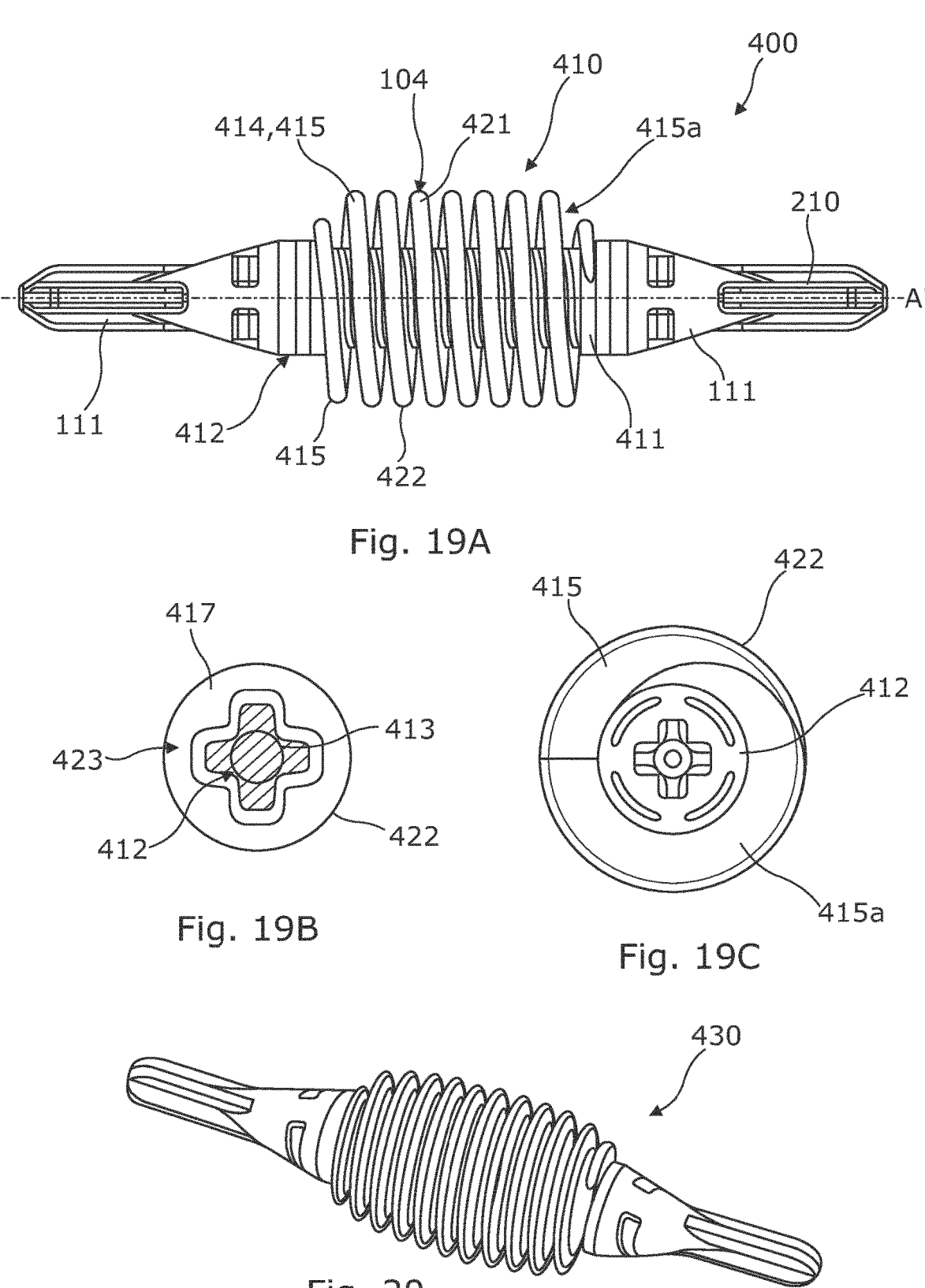
FIG. 19A is a schematic side view of a ninth embodiment of a device.
FIG. 19B is a schematic cross-sectional end view of the device shown in FIG. 19A.
FIG. 19C is a schematic end view of the device shown in FIG. 19A.
FIG. 20 is a schematic perspective view of a tenth embodiment of a brush portion of a device.

Referring now to FIG. 19A, there is shown an embodiment of a device 400. The device 400 comprises a shaft portion 210 shown in FIG. 7. The device 400 further comprises a ninth embodiment of the brush portion 410. The brush portion 410 is generally the same as the embodiment of the brush portion 103 described above so a detailed description will be omitted herein. Furthermore, features and components of the brush portion 410 that are the same as features and components of the brush portion 103 will retain the same terminology and reference numerals.

The brush portion 410 has a longitudinal axis A'. The longitudinal axis A' of the brush portion 410 is coaxial with the longitudinal axis A of the shaft portion 210. The brush portion 410 comprises a core section 411. The core section 411 of the brush portion 410 extends longitudinally across the brush portion receiving section 211 of the shaft portion 210 between the guiding features 111. The core section 411 comprises a central aperture 412, which is best illustrated in the cross-sectional view shown in FIG. 19B. The shaft portion 210 of the device 400 extends through the central aperture 412. The central aperture 412 comprises an internal surface 413. The internal surface 413 of the brush portion 410 is configured to abut the brush portion receiving section 211 of the shaft portion 210. The whole of the internal surface 413 abuts the outer surface brush portion receiving section 211 and the radial projections 213, 225. The core section 411 of the brush portion 410 is generally cylindrical and extends about the core section 212 of the brush portion receiving section 211 of the shaft portion 210.

The brush portion 410 further comprises at least one radial projection 414. The at least one radial projection 414 extends from the core section 411 of the brush portion 410. That is, the at least one radial projection 414 projects radially from the core section 411 in a direction perpendicular to the longitudinal axis A of the shaft portion 210. In addition, the at least one radial projection 414 extends longitudinally along at least a part of the core section 411.

In the present embodiment, the at least one radial projection 414 is formed by at least one helical form 415. The helical form 415 extends radially from the core section 411 of the brush portion 410. The helical form 415 is formed by a projection 414 which is helix shaped. That is, the helical form spirals around the core section 411 of the brush portion 410 such that as it extends circumferentially about the core section 411, it also extends longitudinally. Thus, the plane in which a point of the helical form extends is at an acute angle to the longitudinal axis A' of the brush portion 410.

The helical form 415 is configured to contact a surface of a tubular element for a medicament delivery device during use to lubricate the surface. The helical form 415 may be dimensioned such that it is resiliently compressible and/or resiliently deformable, during use, as discussed above. In general, the shape of the helical form 415 will be configured to match the inner surface of the tubular element to be lubricated. In general, the radius of the helical form 415 is configured such that it forms an interference fit with the surface of the tubular element to be lubricated.

In the present embodiment, the thickness of the helical form 415, i.e., its dimension in the direction parallel to the longitudinal axis A' of the brush portion 410 is constant. However, in alternative embodiments, the thickness of the helical form 415 may vary along the longitudinal axis A' of the brush portion 140.

The helical form 415 comprises a plurality of revolutions. A revolution can be defined as a part of the helical form 415 which extends one full revolution around the longitudinal axis A' of the brush portion 410. In the present embodiment, the helical form comprises eight full revolutions, and eight and a half revolutions in total. However, in an alternative embodiment, the helical form 415 may comprises any number of full and/or partial revolutions. When viewed from the side, the helical form 415 may comprise seven spires, i.e., active contact points furthest from the central axis that are configured to contact and lubricate a surface during movement of the device through a tubular element.

In the present embodiment, the helical form 415 comprises a free end 417. The free end 417 of the helical form 415 is formed by its circumferential surface. The circumferential surface 417 of the helical form 415 is located at a distance from the centreline of the brush portion 410 greater than the distance from the centreline of the shaft portion 210 to the circumferential surface of the guiding features 111 and brush portion receiving portion 211. This ensures that it is the brush portion 410 that contacts a surface of a tubular element to be lubricated instead of the shaft portion 210.

The at least one helical form 415 comprises at least one contact zone 104. The at least one contact zone 104 is located at an end 421 of the helical form 415, which is located distally from the core section 411 of the brush portion 410. The end 421 of the helical form 415 may be formed by the circumferential surface 417. The at least one contact zone 104 comprises at least one contact point 422. The at least one contact point 422 is configured to contact a surface of a tubular element to transfer lubricant agent 106 in the brush portion material 105 to the surface. The contact point 422 may be a point with a small cross-sectional area or a larger area such as the majority of the circumferential surface.

In the present embodiment, the helical form provides a single continuous contact surface. In the present embodiment, the single continuous contact surface is formed by the circumferential surface 417 on the free end of the helical form 415. Furthermore, the brush portion comprises only a single helical form.

Thus, in the present embodiment, there is only one single continuous contact surface of the brush portion that is formed by a single helical form. This single, rigid contact surface is what provides the improved homogeneity of the lubricant agent deposit on the surface of the tubular element. The single continuous contact surface may be more resistant to bending, thus causing more consistent contact with the inner surface of a tubular element for a medicament delivery device. Therefore, in the present embodiment, the helical form also comprises a single continuous contact zone, which is formed by the free end of the helical form at its outer diameter. Furthermore, in the present embodiment, the helical form also comprises a single continuous contact point.

In this embodiment, when contact surfaces, zones, or points are referred to, each of the surfaces, zones, or points are discussed in relation to a given point in the longitudinal direction A'. It will be appreciated that a single surface, zone, or point is present at each given distance in the longitudinal direction and that when each surface, zone, or point is combined with those at each of the other points along the longitudinal direction, a single continuous surface, zone, or point is formed which extends along the brush portion.

As shown in FIG. 19A and FIG. 19C, the contact zone 104 may comprise a single contact point 422 at a given point in the longitudinal direction A'. The contact point 422 may be formed by the distal most portion or extremity 423 of the helical form 415 at any given point in the longitudinal direction A' from the core section 411 of the brush portion 410 in a direction perpendicular to the longitudinal axis A of the shaft portion 210.

In the present embodiment, the contact points 422 of the at least one helical form 415 are spaced from the longitudinal axis A' of the brush portion 210 by a varying distance dependent on the location of the contact point. That is, the outer diameter of the helical form that is formed by the contact points 422 is tapered. In the present embodiment, the outer diameter of the helical form is tapered at both longitudinal ends of the brush portion. The outer diameter of the helical form is tapered such that the outer diameter of the helical form is reduced at the longitudinal ends of the brush portion. For example, the revolution of the helical portion 415 closest to the ends of the brush portion 410 i.e., proximal to the guiding features 111, may be shorter in the radial direction than the other revolutions of the helical form 415. That is, the distance between the longitudinal axis A' and the contact points 422 of the first and last revolutions of the helical form 415 may be shorter than the distance between the longitudinal axis A' and the contact points 422 of the other revolutions of the helical form 415. Essentially, the at least one contact zone 104 at the ends of the brush portion 410 is closer to the longitudinal axis A of the shaft portion 210 than the at least one contact zone spaced from the end of the brush portion 410 in the longitudinal direction.

As shown in FIG. 19A and FIG. 19C, one of the radius of one of revolutions of the helical form 415 increases as the helical form 415 winds about and along the longitudinal axis A'. That is, the helical form 415 begins with a radius equal to the core section 411 and by the time it has completed half a revolution had a radius equal to the other revolutions of the helical form 415. In any of the embodiments described above, this section of the radial projection 234 which is shorter than the rest of the radial projection(s) may be referred to as an introduction chamfer.

Such an arrangement helps guide the device 400 into the tubular element to be lubricated and properly places the device 400 in the tubular element to provide optimum contact for the transfer of lubricant agent 106 from the brush portion material 105 to the inner surface of the tubular element.

However, it will be understood that in an alternative embodiment, the contact points 422 of the at least one helical form 415 may be spaced from the longitudinal axis A' of the brush portion 410 by the same distance at each point along the longitudinal axis A'.

In the present embodiment, the pitch of the helical form 415 is constant. That is, the distance between the start and end of one revolution of the helical form 415 in the longitudinal direction in the same for each revolution of the helical form 415. However, it will be understood that in alternative embodiments the pitch of the helical form 415 may vary in the longitudinal direction.

Referring now briefly to FIG. 20, there is shown a tenth embodiment of the brush portion 430. The brush portion 430 is generally the same as the embodiment of the brush portion 410 described above so a detailed description will be omitted herein. Furthermore, features and components of the brush portion 430 that are the same as features and components of the brush portion 410 will retain the same terminology and reference numerals.

The main difference between the tenth embodiment of the brush portion 430 and the ninth embodiment of the brush portion 410 is that the tenth embodiment of the brush portion comprises a plurality of helical forms. More specifically, in the present embodiment, the brush portion 430 comprises two helical forms.

The operation of a device 100 will now be described with reference to FIG. 23A to FIG. 23C. FIG. 23A shows a device 100 and a tubular element 500 in cross-section. The tubular element 500 is generally cylindrical. The tubular element 500 comprises a first section 501, a second section 502, and a third section 503. The first, second, and third sections 501, 502, 503 are integrally formed. The first, second, and third sections 501, 502, 503 all extend coaxially.

Although the method is described in relation to operation of the first embodiment of the device 100, it will be appreciated that the method is essentially the same for any device formed from a shaft portion and a brush portion within the scope of the present disclosure, such as those described above.

The first section 501 is formed by a first hollow cylinder 505 comprising an open end 506 and an opposing end wall 507. The first hollow cylinder 505 comprises an inner surface 508 which defines an aperture 509. The opposing end wall 507 is annular and comprises a central hole 510.

The second section 502 is formed by a second hollow cylinder 511, which comprises a first open end 512 and a second open end 513. The second hollow cylinder 511 comprises an inner surface 514 which defines an aperture 515. The radius of the aperture 515 in the second hollow cylinder 511 is smaller than the radius of the aperture 509 in the first hollow cylinder 505. However, the radius of the aperture 515 in the second hollow cylinder 511 is equal to the radius of the central hole 510 in the first section 501. The second hollow cylinder 511 extends from the end wall 507 of the first section 501.

The third section 503 is formed by a third hollow cylinder 516, which comprises a first open end 517 and a second open end 518. The third hollow cylinder 516 comprises an inner surface 519, which defines an aperture 520. The third hollow cylinder 516 extends from the open end 513 of the second section 502. However, the radius of the aperture 520 in the third hollow cylinder 516 is larger than the radius of the aperture 515 in the second hollow cylinder 511. Therefore, a step 521 is formed between the second and third sections 502, 503. In addition, the radius of the aperture 520 in the third hollow cylinder 516 is smaller than the radius of the aperture 509 in the first hollow cylinder 505.

In the present embodiment, the inner surface 514 of the tubular element 500 is the surface to be lubricated. The inner surface 514 may have a length in the longitudinal direction of about 30 mm. However, it will be understood that the length of the inner surface 514 may be different. The circumference defined by the inner surface 514 of the tubular element 500 may have a diameter of about 12.5 mm.

The method of lubricating a surface 514 of a tubular element 500 comprises the step of moving a device 100 relative to the tubular element 500. The device 100 is moved into position such that the longitudinal axis A of the shaft portion 102 is aligned with the central longitudinal axis A" of the tubular element 500, as shown in FIG. 23A. In some embodiments, the guiding feature 111*a* of the shaft portion 102 may be gripped, moved, and held by a tool, such as a robot (not shown), to align the device with the tubular element 500.

The method further comprises contacting the tubular element 500 with the brush portion 103 of the device 100. As shown in FIG. 23A, the device 100 is moved along the longitudinal axis A" of the tubular element 500 such that the axle portion 114 of the guiding feature 111 of the shaft portion 102 extends into the aperture 515 defined by the inner surface 514 of the tubular element 500. The device 100 is moved further into the tubular element 500 such that the conical section 117 of the guiding feature 111 of shaft portion 102 enter the aperture 515 of the tubular element 500.

The device 100 is then moved longitudinally until the brush portion 103 of the device 101 enters the tubular element 500. In the present embodiment, the diameter of the aperture 509 of the first section 501 of the tubular element is larger than the radius of the at least one radial projection 234 of the brush portion 103. Therefore, the device 100 is moved further into the tubular element 500 until the first radial projection 234 of the brush portion 103 enters the aperture 515 of the second section 502 of the tubular element 500.

As the circumference of the aperture 515 of the second section 502 of the tubular element 500 is smaller than the diameter of the first radial projection 234 of the brush portion 103 of the device, the contact point 242 of the first radial projection 234 contacts the inner surface 514 of the tubular element 500.

The brush portion material 105 which forms the brush portion 103 is able to resiliently deform under the compressive forces applied to it by the tubular element 500. Thus, the first radial projection 234 may be compressed radially as a result of the smaller diameter of the tubular element 500 and/or may also be resiliently bent in a direction opposite to the direction of movement due to friction between the contact point 242 and the inner surface 514 of the tubular element 500.

The method further comprises releasing lubricant agent 106 from the brush portion 103 of the device 100. The lubricant agent 106 is released from the brush portion material 105 through contact with the inner surface 514 of the tubular element 500. The molecules of the lubricant agent 106 which are not bonded to the brush portion material 105 are free to move from the pores 107 onto the inner surface 514. This is in part because of the difference in concentration of lubricant agent 106 in the brush portion material 105 and on the inner surface 514 of the tubular element 500. Therefore, the lubricant agent 106 exudes from the contact point 242 of the brush portion 103 and is released.

The lubricant agent 106 may be released by virtue of the deformation of the radial projections 234 by the inner surface 514 of the tubular element 500. Thus, as the radial projection 234 is deformed, lubricant agent 106 may be squeezed from the matrix of the brush portion material 105 to the surface of the brush portion 103, more specifically towards the contact point 242.

The method further comprises the step of depositing the lubricant agent 106 on the surface of the tubular element 500. Thus, as the molecules of lubricant agent 106 exude out of the contact point 242 of the radial projection 234, the relative movement of the device 100 to the inner surface 514 transfers the lubricant agent 106 on the inner surface 514 of the tubular element 500. That is, the depositing of lubricant agent 106 on the inner surface 514 of the tubular element 500 is driven by the cumulative radial force exerted on the inner surface 514 of the tubular element 500 and the axial force linked to friction. The maximum radial force experienced by a single radial projection 234 may be in the region of 25 N to 60 N. For instance, the maximum radial force experienced by a single radial projection 234 may be in the range of 35 N to 60 N in the first cycle, or in the range of 50 N to 60N. For instance, the minimum radial force experienced by a single radial projection 234 may be in the range of 20 N to 40 N in the first cycle, or in the range of 20 N to 35 N. These ranges are not applicable to radial projections, which form a part of the introduction chamfer section of the brush portion 103.

As the device 500 is moved further through the tubular element 500, each of the subsequent radial projections 234 of the brush portion 103 contact the inner surface 514 if the tubular element 500. The frictional force opposing movement of the subsequent radial projections 234 of the brush portion 103 against the inner surface 514 of the tubular element 500 may be less than for the previous radial projection 234 due to the lubricant agent 106 deposited on the inner surface 514 of the tubular element 500 by the previous radial projection 234.

The method described above occurs sequentially for each of the radial projections 234 as they are moved into contact with the inner surface 514 of the tubular element 500. The device 100 is moved continually until each of the radial projections 234 have been moved across the whole of the inner surface 514 of the tubular element 500 in the longitudinal direction, as shown in FIG. 23C.

The device 100 may be moved through the tubular element 500 at a speed of between about 0.1 m/s to about 1.6 m/s. The speed of the device 100 may reduce as the number of contact points 242 in contact with the inner surface 514 of the tubular element increases as the device 100 enters the tubular element 500, due to an increase in friction, and may then increase as the number of contact points 242 in contact with the inner surface 514 of the tubular element 500 decreases as the device 100 leaves the tubular element 500, due to a decrease in friction.

As shown in FIG. 23A to FIG. 23C, the device 100 may be moved in a first direction, for example left to right in the Figures, relative to the inner surface 514 of the tubular element 500 whilst in contact with the inner surface 514 of the tubular element 500. A tool (not shown) may then collect the device 100 once it has passed through the tubular element 500. The tool may return the device 100 to the original start position shown in FIG. 23A to pass through the same tubular element 500 or a different tubular element 500.

Alternatively, the device may be additionally moved in a second direction, for example right to left in the Figures, relative to the inner surface 514 of the tubular element 500 whilst in contact with the inner surface 514 of the tubular element 500, after being moved through the tubular element 500 in a first direction.

In some embodiments, when the device 100 is moved in the second direction, the orientation of the device 100 remains unchanged. Thus, the leading guiding element 111*a* in the first direction becomes the trailing guiding feature 111*a* when the device 100 is moved in the second direction. This has the advantage of reducing the wear on the leading radial projections 234 and extends the life of the device 100. This enables the device 100 to perform up to 900 cycles before the axial force on the radial projections 234 becomes too low to effectively transfer lubricant agent 106 to the inner surface 514 of the tubular element 500.

In other embodiments, when the device 100 is moved in the second direction, the device 100 may be rotated 180 degrees such that the leading guiding feature 111*a* when the device is moved in the first direction is also the leading guiding feature 111*a* when the device is moved in the second direction through the tubular element 500.

The method may comprises moving the device 100 mechanically using a tool, such as a robot (not shown). In addition or alternatively, the method may comprises moving the device 100 relative to the tubular element 500 using a pressure difference applied thereto. For example, an at least partial vacuum may be applied in front of the device 100 in the aperture 515 of the tubular element 500. The vacuum may be maintained because the radial projections 234 may effectively form a seal against the inner surface 514 of the tubular element 500. Alternatively, a positive pressure may be applied behind the device 100.

The depositing step may comprise depositing a layer of lubricant agent 106 on the inner surface 514 of the tubular element 500 that is in the range of about 40 nm to 60 nm thick. In this case, the thickness of the layer is measured perpendicularly to and from the inner surface 514 of the tubular element 500.

Using the above described method and a device as described in relation to FIG. 19A to 19C, the inventors have found that using a brush portion 410 formed by a thermoplastic elastomer and impregnated with a lubricant agent such that the weight of each compound accounts for roughly 50% of the total weight of the brush portion 410 gives a brush portion 410 defined by a Young's Modulus of 2400 MPa for the brush portion material and 40 MPa for the lubricant agent. Such a brush portion 410 has a co-efficient of friction with an inner surface of a hollow tube in the range of 0.08.

The exemplary device described above comprised an outer diameter of 13.1 mm and was moved through a tubular element to determine the axial force required to move the device. The tubular element had a nominal diameter of 12.52 mm, ranging from 12.49 mm to 12.57 mm. In the example described, the force required to move the device at a constant velocity of 1 m/s had a nominal value of 30.6 N, ranging from 29.1 N, when the pipe diameter was largest, and 31.6 N, when the pipe diameter was at its smallest.

In other experiments, it was found that the exemplary embodiment met the design conditions of the device requiring an initial axial force of 35 N to be moved through the tubular element at 1 m/s and requiring an axial force of at least 25 N to be moved through the tubular element at 1 m/s after 900 cycles. Thus, the axial force, which is related to the frictional force between the device and tubular element, does not deplete completely. Consequently, it can be assumed that there is still sufficient contact between the brush portion and the tubular element to provide adequate lubrication.

Thus, in some embodiments, the axial force required to move the device through a hollow tubular element may be approximately 30 N, or in the range of about 25N to about 35 N. More specifically, the axial force required to move the device through a hollow tubular element at 1 m/s may be approximately 35 N for the first cycle and approximately 25 N for the 900 cycle. That is, in some embodiments, the axial force required to move the device through a hollow tubular element after 900 cycles is within approximately 10N to 15N of the axial force initially required to move the device through a hollow tubular element.

The exemplary device described above was also moved through a tubular element to determine whether it met the targets of cumulative radial force required. The inventors found that for the exemplary device with eight revolutions that are active with two at least partial revolutions that are not active due to smaller radii, the initial radial force experienced by the active portions of the helical form was about 54 N, or in the range of 50 N to 60N.

In total, the target cumulative radial force experienced by the contact points along a line extending parallel to the longitudinal axis of the device was roughly 415 N. The target cumulative radial force to be experiences after 900 cycles was at least roughly 310 N. The exemplary device described above experiences a cumulative radial force of roughly 370 N after 900 cycles. This was mainly due to the contact points on the revolutions at the extremes of the brush portion being damaged upon entry into the tubular portion. In some experiments, as much as 25 N to 40 N less force was felt by the each of the revolutions at either end of the brush portion whilst the radial force experienced by the other revolutions change minimally.

Thus, in some embodiments, the cumulative radial force applied by a single contact point on a full radius revolution of the helical form of the device to a hollow tubular element may initially be approximately 55 N, or in the range of about 50N to about 60 N. In an embodiment with 8 full revolutions, the cumulative radial force applied after 900 cycles may be at least approximately 370 N. In an embodiment with 10 full revolutions, the cumulative radial force applied after 900 cycles may be at least approximately 480 N.

In some embodiments, the cumulative radial force applied by the device with a single helical form on a hollow tubular element after 900 cycles is within approximately 40N to 50N of the initial cumulative radial force applied by the device with a single helical form on a hollow tubular element. That is, in some embodiments, the force experienced after 900 cycles is at most 50N less than the initial force.

Figure 24:
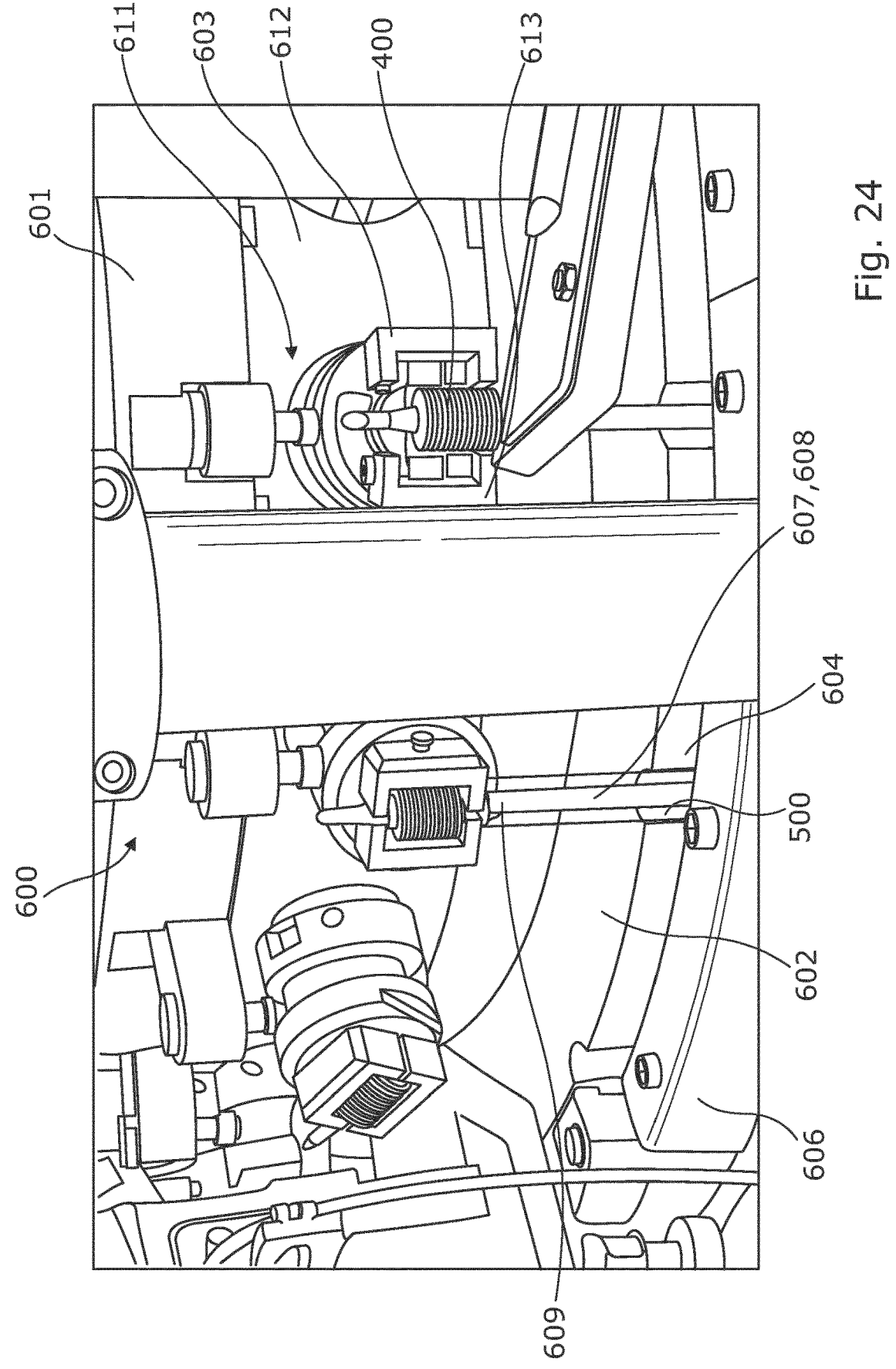
FIG. 24 is a schematic perspective side view of an apparatus for lubricating a tubular element for a medicament delivery device.

Referring briefly to FIG. 24, an embodiment of an apparatus 600 for performing the method of lubricating a surface 514 of a tubular element 500, is shown. The apparatus 600 comprises a rotatable drum 601. The drum 601 has a central axis about which the drum 601 is rotatable. In the present embodiment, the central axis of the drum 601 extends substantially perpendicularly.

The drum 601 comprises a first section 602 and a second section 603. The first section 602 has a larger diameter than the second section 603. The drum 601 further comprises a tubular element receiving section 604, which is configured to receive a tubular element 500 during use. The tubular element receiving section 604 is located in the first section 602 of the drum 601.

The tubular element receiving section 604 comprises a generally semi-circular recess in the circumferential surface 605 of the first section 602 of the drum 601. The tubular element 514 is at least partially received in the tubular element receiving section 604 during use. The first section 602 of the drum 601 may comprise a plurality of tubular element receiving sections 604 that are spaced circumferentially about the first section 602 of the drum 601.

The apparatus 600 may further comprise a guide rail 606. The guide rail 606 extends circumferentially around at least a part of the circumference of the first section 602 of the drum 601. The guide rail 606 is configured to help retain the tubular element 500 in the tubular element receiving section 604. In some embodiments, the guide rail 606 may contact the tubular element 500 with enough force to cause the tubular element to rotate as it is moved around the circumference of the drum 601. This causes relative rotation between the device 400 and the tubular element 500, which helps to lubricate the interior surface of the tubular element 500.

The apparatus 600 further comprises a device manipulator 607. The device manipulator 607 is rotatable about the central axis of the drum 601 together with the first section 602 of the drum 601. The device manipulator 607 comprises a movable rod 608. The rod 608 is configured to be moved in a direction substantially parallel to the central axis about which the drum rotates. The rod 608 may be moveable by, for example, pneumatics, hydraulics, or mechanically, and in some embodiments may be telescopic.

The device manipulator 607 may further comprise a device handler 609 at one end of the rod 608. The device handler 609 comprises a hollow end of the rod 608 configured to receive the shaft portion 210, specifically the axle portion 114 of the guiding feature 111. The device handler 609 may be profiled to match the cross-section of the extremity of the axle portion 114. This allows the device manipulator 607 to orientate the device 400 and either rotate the device 400 or the resist rotation of the device 500 caused by rotation of the tubular element 500. That is, the device manipulator may move the device relative to the tubular element 500 by translational movement only. In other embodiments, the device manipulator may moving the device relative to the tubular element 500 by translational and rotational movement. The rotational movement of the device about its axis relative to the inner surface of the tubular element as it passes through the tubular element being lubricated may also provide an improved homogenous lubrication of inside surface of the tubular element.

In the present embodiment, the device manipulator 607 receives a device 400 in the device handler 609 at one end of the tubular element 500, i.e., the bottom end of the tubular element 500 in the Figure, as the drum 601 rotates. As the drum 601 continues to rotate, a tubular element 500 is received in the tubular element receiving section 604. The rod 608 is then actuated to push the device 400 through the tubular element 500 as the device manipulator 607 and drum 601 rotate at the same angular velocity. The rod 608 pushes the device 400 through the tubular element 500 until the device handler 609 moves out of the top end of the tubular element 500. In some embodiments, the apparatus 600 comprises a plurality of device manipulators, for example, one device manipulator 607 per tubular element receiving section 604.

The drum 601 further comprises an orientating tool 611. The orientating tool 611 is configured to take over control of the device 400 once it has been pushed through the tubular element 500. The orientation tool 611 comprises two clamping hands 612, 613. The clamping hands 612, 613 are generally U-shaped and configured to grip the guiding feature 111 of the shaft portion 210, specifically the conical section 117. The clamping hands 612, 613 are movable from an open position, in which the device 400 can be placed in between them by the device manipulator 609, to a closed position in which the clamping hands 612, 613 grip the device 400. In some embodiments, the apparatus 600 comprises a plurality of orientating tools, for example, one orientating tool 611 per tubular element receiving section 604.

The orientating tool 611 extends from the second section 603 of the drum 601 such that the orientating tool 611 is located directly above the tubular element receiving section 604 and device manipulator 607. The orientating tool 611 is configured to rotate about an axis that extends perpendicularly relative to the central axis of the drum 601. Once the clamping hands 612, 613 have gripped the device 400, the orientating tool 611 rotates the device 180 degrees so that it is ready to be moved through another tubular element 500 but in the opposite direction. In order to achieve this, the device manipulator 607 is extended through a tubular element 500 to grip the device 400 and pull it down through the tubular element. The apparatus 600 may further comprise another orientating tool at the bottom end of the tubular element so turn the device 400 again. Thus, the device 400 can be continually moved up and down through a plurality of tubular elements as it rotates around the drum 601.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A method of lubricating a surface of a tubular element for a medicament delivery device, the method comprising the steps of:
   moving a device relative to the tubular element for the medicament delivery device;
   contacting the tubular element with a brush portion of the device, the brush portion being formed from a brush portion material and a lubricant agent; and
   depositing lubricant agent on the surface of the tubular element to lubricate a surface of the tubular element by deforming the brush portion through contact with the tubular element to release the lubricant agent.

2. The method according to claim 1, wherein the device and the tubular element are moved continuously along an arcuate path about a rotational axis of a lubricating apparatus whilst in contact with each other.

3. The method according to claim 1, wherein the device and the tubular element are moved continuously along an arcuate path about a rotational axis of a lubricating apparatus whilst in contact with each other.

4. The method according to claim 1, wherein the moving step comprises moving the device using a translation movement relative to the tubular element.

5. The method according to claim 4, wherein the moving step further comprises moving the device using a rotational movement relative to the tubular element.

6. The method according to claim 1, wherein the depositing step comprises depositing a layer of lubricant on the surface of the tubular element, the layer comprising a thickness in the range of about 40 nanometers (nm) to about 60 nm.

7. The method according to claim 1, wherein the step of moving the device comprises moving the device into a position such that a longitudinal axis of a shaft portion of the device is aligned with a central axis of the tubular element.

8. The method according to claim 7, wherein the step of moving the device comprising moving the device into the tubular element such that an introduction chamfer of the brush portion contacts the surface of the tubular element to align the longitudinal axis of the shaft portion with the central axis of the tubular element.

9. The method according to claim 1, wherein the step of moving the device comprising moving the device into the tubular element such that an introduction chamfer of the brush portion contacts the surface of the tubular element to align a longitudinal axis of a shaft portion of the device with a central axis of the tubular element.

10. The method according to claim 1, wherein the device is moved mechanically by an arm of a lubricating apparatus.

11. The method according to claim 1, wherein the device is moved by a pressure difference applied thereto.

12. The method according to claim 1, wherein the device is moved in a single direction relative to the surface of the tubular element whilst in contact with the surface of the tubular element.

13. The method according to claim 12, wherein the device is rotated 180 degrees about an axis perpendicular to a longitudinal axis of the device between movements in the single direction.

14. The method according to claim 1, wherein the device is moved in a first direction relative to the surface of the tubular element whilst in contact with the tubular element and in a second direction relative to the tubular element whilst in contact with the tubular element.

15. The method of claim 14, wherein the second direction is the opposite direction to the first direction.

16. The method according to claim 14, wherein the device is rotated 180 degrees about an axis perpendicular to a longitudinal axis of the device between movements in the first and second directions.

17. The method according to claim 1, wherein the device is moved at a speed of between about 0.1 m/s to about 1.6 m/s.

18. The method according to claim 1, wherein a maximum radial force experienced by a single radial projection or revolution is between about 25 Newtons (N) to about 60N.

19. The method according to claim 18, wherein a minimum radial force experienced by a single radial projection or revolution is between about 20N to about 40N.

20. The method according to claim 1, wherein the brush portion is impregnated with the lubricant agent.

* * * * *